US009295269B2

(12) United States Patent
Clarke et al.

(10) Patent No.: US 9,295,269 B2
(45) Date of Patent: Mar. 29, 2016

(54) CONFECTIONERY PRODUCT CONTAINING ACTIVE AND/OR REACTIVE COMPONENTS AND METHODS OF PRODUCTIONS THEREOF

(75) Inventors: Peter Clarke, Berkshire (GB); Sarah Marshall, West Berkshire (GB)

(73) Assignee: READING SCIENTIFIC SERVICES LIMITED (GB)

( * ) Notice: Subject to any disclaimer, the term of this patent is extended or adjusted under 35 U.S.C. 154(b) by 625 days.

(21) Appl. No.: 13/583,308

(22) PCT Filed: Mar. 23, 2011

(86) PCT No.: PCT/GB2011/050587
§ 371 (c)(1),
(2), (4) Date: Nov. 15, 2012

(87) PCT Pub. No.: WO2011/117634
PCT Pub. Date: Sep. 29, 2011

(65) Prior Publication Data
US 2013/0101649 A1      Apr. 25, 2013

Related U.S. Application Data

(60) Provisional application No. 61/316,428, filed on Mar. 23, 2010.

(30) Foreign Application Priority Data

Mar. 23, 2010   (GB) .................................. 1004890.8

(51) Int. Cl.
| | |
|---|---|
| *A23G 3/50* | (2006.01) |
| *A23G 3/00* | (2006.01) |
| *A23G 4/20* | (2006.01) |
| *A23G 3/54* | (2006.01) |
| *A23G 1/54* | (2006.01) |
| *A61K 8/02* | (2006.01) |
| *A23G 3/36* | (2006.01) |
| *A23G 4/12* | (2006.01) |
| *A23L 1/00* | (2006.01) |
| *A23L 1/22* | (2006.01) |

(52) U.S. Cl.
CPC .. *A23G 3/54* (2013.01); *A23G 1/54* (2013.01); *A23G 3/364* (2013.01); *A23G 4/12* (2013.01); *A23G 4/20* (2013.01); *A23L 1/0079* (2013.01); *A23L 1/22008* (2013.01); *A61K 8/0216* (2013.01)

(58) Field of Classification Search
None
See application file for complete search history.

(56) References Cited

U.S. PATENT DOCUMENTS

| | | | |
|---|---|---|---|
| 1,556,617 A | 10/1925 | Laskey et al. | |
| 2,284,651 A | 6/1942 | Gundlach et al. | |
| 3,644,169 A | 2/1972 | Phillips | |
| 4,032,661 A | 6/1977 | Rowsell et al. | |
| 4,136,163 A | 1/1979 | Watson et al. | |
| 4,230,688 A | 10/1980 | Rowsell et al. | |
| 4,459,425 A | 7/1984 | Amano et al. | |
| D288,380 S | 2/1987 | Eldred et al. | |
| 4,679,496 A | 7/1987 | Simelunas et al. | |
| 4,925,380 A | 5/1990 | Meisner | |
| 4,932,317 A | 6/1990 | Hoormann | |
| 5,017,385 A | 5/1991 | Wienecke | |
| 5,227,154 A | 7/1993 | Reynolds | |
| 5,266,592 A | 11/1993 | Grub et al. | |
| 5,300,305 A | 4/1994 | Stapler et al. | |
| 5,378,131 A | 1/1995 | Greenberg | |
| 5,439,695 A | 8/1995 | Mackey | |
| 5,888,567 A | 3/1999 | Daouse | |
| 5,955,116 A | 9/1999 | Kehoe et al. | |
| 6,235,318 B1 | 5/2001 | Lombardy, Jr. et al. | |
| 6,471,945 B2 | 10/2002 | Luo et al. | |
| 6,479,071 B2 | 11/2002 | Holme et al. | |
| 6,485,739 B2 | 11/2002 | Luo et al. | |
| 6,627,233 B1 | 9/2003 | Wolf et al. | |
| 6,685,916 B1 | 2/2004 | Holme et al. | |
| 6,696,044 B2 | 2/2004 | Luo et al. | |
| 6,733,818 B2 | 5/2004 | Luo et al. | |
| 6,780,443 B1 | 8/2004 | Nakatsu et al. | |
| 6,846,500 B1 | 1/2005 | Luo et al. | |
| 6,949,264 B1 | 9/2005 | McGrew et al. | |
| 7,112,345 B1 | 9/2006 | McHale et al. | |

(Continued)

FOREIGN PATENT DOCUMENTS

| | | |
|---|---|---|
| CN | 2174851 Y | 8/1994 |
| EP | 0775446 A2 | 5/1997 |

(Continued)

OTHER PUBLICATIONS

Vanillyl alcohol, Food and Flavor Ingredient, Flavis No. 2.213 | Sigma-Aldrich; downloaded online Apr. 22, 2015.*
International Search Report; International Application No. PCT/GB2011/050587; Date of Completion of International Search Sep. 28, 2011; 5 pages.
Code of Federal Regulations, Title 21, Section 172.615 Chewing Gum Base, Apr. 1, 2009 Edition, 4 pages.

(Continued)

*Primary Examiner* — Michael G Hartley
*Assistant Examiner* — Nabila Ebrahim
(74) *Attorney, Agent, or Firm* — Cantor Colburn LLP

(57) ABSTRACT

The invention relates to a confectionery product comprising an extruded body portion, the body portion having a plurality of capillaries disposed therein, one or more of the capillaries being at least partially filled with a fill material which is a different material from that of the extruded body portion, the fill material and optionally the body portion comprising various active and/or reactive components. Some embodiments are designed to provide sequential release profiles. The invention also relates to a process for the manufacture of the same.

13 Claims, 12 Drawing Sheets

(56) References Cited

U.S. PATENT DOCUMENTS

| | | |
|---|---|---|
| 2002/0136812 A1 | 9/2002 | Degady et al. |
| 2003/0059501 A1 | 3/2003 | Rivier |
| 2003/0215417 A1 | 11/2003 | Uchiyama et al. |
| 2004/0081713 A1 | 4/2004 | Maxwell et al. |
| 2004/0086615 A1* | 5/2004 | Johnson et al. ............... 426/548 |
| 2004/0136928 A1 | 7/2004 | Holme et al. |
| 2004/0167039 A1* | 8/2004 | Ahmad et al. ............... 508/220 |
| 2004/0206246 A1 | 10/2004 | Bortone et al. |
| 2004/0265455 A1 | 12/2004 | Wray et al. |
| 2005/0008732 A1 | 1/2005 | Gebreselassie et al. |
| 2005/0025721 A1 | 2/2005 | Holme et al. |
| 2005/0025879 A1 | 2/2005 | Jury |
| 2005/0118304 A1 | 6/2005 | Rasmussen |
| 2005/0202118 A1* | 9/2005 | Johnson et al. ............... 426/3 |
| 2006/0280837 A1 | 12/2006 | Jani et al. |
| 2007/0003663 A1 | 1/2007 | Jani et al. |
| 2007/0031535 A1 | 2/2007 | Robinson |
| 2007/0275119 A1 | 11/2007 | Lakkis |
| 2008/0050483 A1 | 2/2008 | Fornaguera |
| 2008/0095899 A1 | 4/2008 | Fornaguera |
| 2010/0216830 A1* | 8/2010 | Iyoha et al. ............... 514/289 |
| 2011/0217427 A1 | 9/2011 | Vaman et al. |
| 2011/0293795 A1 | 12/2011 | Vaman et al. |
| 2013/0101707 A1 | 4/2013 | Clarke et al. |
| 2013/0108740 A1 | 5/2013 | Clarke et al. |

FOREIGN PATENT DOCUMENTS

| | | |
|---|---|---|
| EP | 1151673 A1 | 1/2002 |
| GB | 226006 | 12/1924 |
| GB | 549427 A | 11/1942 |
| GB | 1505491 | 3/1978 |
| GB | 2307165 A | 5/1997 |
| JP | 49125562 A | 12/1974 |
| JP | 5157859 A | 5/1976 |
| JP | 53142565 A | 12/1978 |
| JP | 5414556 A | 2/1979 |
| JP | 62079736 | 4/1987 |
| JP | 08009887 | 1/1996 |
| JP | 09051789 | 2/1997 |
| JP | 09163932 A | 6/1997 |
| JP | 2000210024 A | 8/2004 |
| JP | 3118586 U | 1/2006 |
| RU | 52669 U1 | 4/2006 |
| WO | 0025598 | 5/2000 |
| WO | 2004068964 A1 | 8/2004 |
| WO | 2005056272 A1 | 6/2005 |
| WO | 2006016128 A1 | 2/2006 |
| WO | 2007044628 A1 | 4/2007 |
| WO | 2007056685 A2 | 5/2007 |
| WO | 2008044122 A2 | 4/2008 |
| WO | 2008045579 A1 | 4/2008 |
| WO | 2008048881 A2 | 4/2008 |
| WO | 2009108769 A2 | 9/2009 |
| WO | 2010034973 A1 | 4/2010 |
| WO | 2010034977 A1 | 4/2010 |
| WO | 2010034979 A1 | 4/2010 |
| WO | 2010034980 A1 | 4/2010 |
| WO | 2010034981 A1 | 4/2010 |
| WO | 2011117635 A1 | 9/2011 |
| WO | 2011117639 A1 | 9/2011 |
| WO | 2011117640 A1 | 9/2011 |
| WO | 2012098401 A1 | 7/2012 |
| WO | 2013042028 A1 | 3/2013 |
| WO | 2013402028 A1 | 3/2013 |

OTHER PUBLICATIONS

U.S. Appl. No. 60/618,222, filed with the USPTO on Oct. 13, 2004.
DE19907782 A1, filed on Feb. 24, 1999, Abstract Only, 1 page.
Extended European Search Report for European Application No. 12178340.1-2114, European Filing Date Jul. 27, 2012, Date of Report Oct. 16, 2012, 5 pages.
Fr 247728 A1, abstract only, Jul. 16, 1982.
GB Search Report; Application No. GB0817366.8; Date of Search: Dec. 29, 2008; 4 pages.
GB Search Report: Application No. GB0817367.6; Date of Search Jan. 9, 2009; 4 pages.
Hunter et al., "Calcium channel blockers 1: review of their mechanisms of action", Pharmacy International, Nov. 1985, p. 267-271.
International Search Report and Written Opinion of PCT/GB2009002248, mailing date Dec. 30, 2009, 17 pages.
International Search Report for PCT/GB2009002258, mailing date Dec. 15, 2009, 3 pages.
JP08009887; filed on Jun. 29, 1994; Abstract Only; 1 page.
JP61162135 A, filed on Jan. 9, 1985, Abstract Only, 1 page.
Manly et al., "Substances Capable of Decreasing the Acid Solubility of Tooth Enamel", Journal of Dental Research, 1949, vol. 28 No. 2, p. 160-171.
International Application No. PCT/GB2009/002248; International Filing Date: Sep. 22, 2009; Priority Document; GB0817366.8 filed Sep. 23, 2008; 59 pages.
International Application No. PCT/GB2009/002258; International Filing Date Sep. 22, 2009; Priorty Document: GB0817367.6 filed Sep. 23, 2008, 81 pages.
WO9727760 A1; filed on Feb. 3, 1997, Abstract Only; 1 page.
Zhang, Zhongsheng; "Introduction of Manufacture Process of Typical Filled Confections"; Food Science, Issue 7, 1984, pp. 31-35. (English Machine Translation).
Liang, Yinghong; "The development of a new type of filled confections"; Science and Technology of Food Industry; vol. 22, No. 6, 2001, pp. 64-65. (English Machine Translation).
Written Opinion for International Application No. PCT/GB2011/050587, International Filing Date Mar. 23, 2011, Date of Mailing Jan. 30, 2012, 9 pages.

* cited by examiner 10 mm 10 mm 10 mm 10 mm

CIRCA 10 mm
MATERIAL 2

CIRCA 10 mm
MATERIAL 2

CONFECTIONERY PRODUCT CONTAINING ACTIVE AND/OR REACTIVE COMPONENTS AND METHODS OF PRODUCTIONS THEREOF

CROSS REFERENCE TO RELATED APPLICATIONS

This is a US National Stage of Application No. PCT/GB2011/050587, filed on Mar. 23, 2011, which claims the benefit of GB Application No. 1004890.8 filed Mar. 23, 2010 and U.S. Provisional Application No. 61/316,428 filed Mar. 23, 2010, the disclosures of which are incorporated herein by reference.

TECHNICAL FIELD OF THE INVENTION

The present invention relates to confectionery and method of production thereof. In particular, the invention relates to confectionery comprising one or more capillaries which may contain a fluid or other material.

BACKGROUND TO THE INVENTION

It is desirable to produce confectionery formed of different components, so as to increase sensory pleasure. A number of confectionery products exist, which have a flavoured liquid or syrup centre which is released upon chewing. For example, WO2007056685 discloses an apparatus and method for the continuous production of centre-filled confectionery products in the format of a continuous extrudate having a plurality of centre-filled confectionery ropes. Whilst a product formed from such an apparatus does increase sensory pleasure, the period of pleasure is often short lived as the centre is released quickly and/or degraded. Some embodiments of the present invention can provide a confectionery product which can release a fluid centre over an extended period of time.

There is also a demand for providing confectionery having a reduced fat or sugar content. Some embodiments of the present invention can provide a confectionery product which can be produced having a lowered fat or sugar content, whilst still maintaining an excellent sensory pleasure.

It is an aim of an embodiment or embodiments of the present invention to overcome one or more of the problems of the prior art. It is also an aim of some embodiments of the present invention to provide a confectionery having an extended fluid fill release profile and a method of manufacture thereof. It is also a further aim of some embodiments of the present invention to provide a confectionery which has a reduced fat and/or sugar profile and a method of manufacture thereof.

SUMMARY OF THE INVENTION

According to an embodiment of the present invention, there is provided a confectionery product comprising an extruded body portion, the body portion having a plurality of capillaries disposed therein, one or more of the capillaries being at least partially filled with a fill material which is a different material from that of the extruded body portion, the fill material comprising an active and/or reactive component and wherein two or more different active/reactive components are provided in the same or different capillaries.

The present invention therefore provides for a confectionery product which can be used in confectionery having an extended release of one or more materials inserted into the capillaries, or a confectionery product having a large voidage so as to reduce the amount confectionery material used in the product, whilst maintaining the overall size of the product.

It should be understood that the term "plurality" is intended to mean two or more. In some embodiments, a plurality is 3 or more, or 4 or more, or 5 or more, or 6 or more, or 7 or more. There is no particular upper limit on the number associated with "plurality". In the context of the phrase "plurality of capillaries", numbers up to 50 and higher are contemplated.

It should be understood that the term "capillary" generally refers to a conduit or space created by an extrusion or other forming process within the body of the product. The capillary typically contains matter, and that matter can be in the form of a gas, a liquid, a solid, or a mixture thereof.

It should be understood that the term "voidage" generally refers to the volume percent of the capillary volume relative to the sum of the capillary volume and the extruded body portion volume. That is voidage (%)=100×capillary volume/(capillary volume+extruded body portion volume). In some embodiments, the extruded body portion volume does not include any central region volume created by certain dies, such as an annular die.

In some embodiments, the capillaries disposed in the extruded body portion can be at least partially filled with one or more fill materials, such as, but not limited to, liquid fill materials. The fill materials contained in the capillaries may be homogenously or non-homogenously mixed. The capillaries each may contain one or more fill materials that are the same or different and different capillaries may contain fill materials with different colors, flavors, flavor combinations, color combinations, flavor intensities, color intensities, viscosities, solubilities, densities, textures, fill percentages, materials, material combinations (e.g., combinations of liquid and suspended particulates within the liquid), material ratios, functional strengths, aftertastes, sensory profiles, temporal profiles, mechanisms of action (chemical, mechanical, trigeminal, receptor, exothermic, endothermic), locations of action (e.g. tongue, throat), odors, hydrophobicities, hygrophobicities, water activities, barrier properties, reactions to air and/or water, chemical stabilities, changes over time (e.g., solid to liquid, liquid to solid), shelf life characteristics, crystal structures, etc.

In some embodiments, liquid fill materials can include particulates suspended therein, such as, but not limited to, sugars, fruit pieces, nut pieces, powdered ingredients and the like.

In some embodiments, two or more capillaries may have the same or different size, cross-section (e.g., circle, oval, square, triangular, star-shaped), cross-sectional area, circumference, etc. One or more capillaries also may be continuous or discontinuous within the body portion.

A single capillary may contain one or more active/reactive components and different capillaries may contain the same or different components, combinations of components, ratios of components, etc.

By providing a product which may have two or more capillaries at least partially filled with different fill materials, the confectionery product can have different taste, temporal, sensory and/or texture profiles at different parts of the product or during consumption.

The two or more different active/reactive components may be configured in the capillaries so that the different components are mixed together when the product is consumed. If desired, the active/reactive component may be activated by consumption of the confectionery product. Such activation may be the mixing of two different compounds located in two different capillaries, or the activation of a compound by contact with saliva.

Two or more capillaries may be at least partially filled with different fill materials.

The active and/or reactive component may be encapsulated. The skilled addressee will be aware of a range of compositions which are used in encapsulating active and/or reactive compositions in confectionery.

An "active/reactive component" may be selected from any one or more of the following: flavour agents; oral care actives and other functional ingredients; sweetening agents; physiological cooling agents; warming agents; tingling agents; colouring agents; effervescence agents, pharmaceutical agents, nutraceutical agents, botanical extracts, teeth whitening agents and combinations thereof. Such agents will be apparent to the skilled addressee.

More particularly, active/reactive components may include, but are not limited to: colour and flavour, multiple flavours, multiple colours, cooling agent and flavour, warming agent and flavour, cooling agent and warming agent, cooling agent and high intensity sweetener, warming agent and high intensity sweetener, multiple cooling agents (e.g., WS-3 and WS-23, WS-3 and menthyl succinate), menthol and one or more cooling agents, menthol and one or more warming agents, multiple warming agents, high intensity sweetener(s) and tooth whitening active(s), high intensity sweetener(s) and breath freshening active(s), an ingredient with some bitterness and a bitterness suppressor for the ingredient, multiple high intensity sweeteners (e.g., ace-k and aspartame), multiple tooth whitening actives (e.g., an abrasive ingredient and an antimicrobial ingredient, a peroxide and a nitrate, a warming agent and a polyol, a cooling agent and a polyol, multiple polyols, a warming agent and micronutrient, a cooling agent and a micronutrient, a warming agent and a mouth moistening agent, a cooling agent and a mouth moistening agent, a warming agent and a throat care agent, a cooling agent and a throat care agent, a warming agent and a food acid, a cooling agent and food acid, a warming agent and an emulsifier/surfactant, a cooling agent and an emulsifier/surfactant, a warming agent and a color, a cooling agent and a color, a warming agent and a flavor potentiator, a cooling agent and a flavor potentiator, a warming agent with sweetness potentiator, a cooling agent with a sweetness potentiator, a warming agent and an appetite suppressant, a cooling agent and an appetite suppressant, a high intensity sweetener and a flavor, a cooling agent and a teeth whitening agent, a warming agent and a teeth whitening agent, a warming agent and breath freshening agent, a cooling agent and a breath freshening agent, a cooling agent and an effervescing system, a warming agent and an effervescing system, a warming agent and an antimicrobial agent, a cooling agent and an antimicrobial agent, multiple anticalculus ingredients, multiple remineralization ingredients, multiple surfactants, remineralization ingredients with demineralization ingredients, acidic ingredients with acid buffering ingredients, anticalculus ingredients with antibacterial ingredients, remineralization ingredients with anticalculus ingredients, anticalculus ingredients with remineralization ingredients with antibacterial ingredients, surfactant ingredients with anticalculus ingredients, surfactant ingredients with antibacterial ingredients, surfactant ingredients with remineralization ingredients, surfactants with anticalculus ingredients with antibacterial ingredients, multiple types of vitamins or minerals, multiple micronutrients, multiple acids, multiple antimicrobial ingredients, multiple breath freshening ingredients, breath freshening ingredients and antimicrobial ingredients, multiple appetite suppressors, acids and bases that react to effervesce, a bitter compound with a high intensity sweetener, a cooling agent and an appetite suppressant, a warming agent and an appetite suppressant, a high intensity sweetener and an appetite suppressant, a high intensity sweetener with an acid, a probiotic ingredient and a prebiotic ingredient, a vitamin and a mineral, a metabolic enhancement ingredient with a macronutrient, a metabolic enhancement ingredient with a micronutrient, an enzyme with a substrate, a high intensity sweetener with a sweetness potentiator, a cooling compound with a cooling potentiator, a flavor with a flavor potentiator, a warming compound with a warming potentiator, a flavor with salt, a high intensity sweetener with salt, an acid with salt, a cooling compound with salt, a warming compound with salt, a flavor with a surfactant, an astringent compound with an ingredient to provide a sensation of hydration, etc. In some embodiments, the multiple ingredients may be part of the same delivery system or may be part of different delivery systems.

Sensate compounds can include cooling agents, warming agents, tingling agents, effervescent agents, and combinations thereof. A variety of well known cooling agents may be employed. For example, among the useful cooling agents are included xylitol, erythritol, dextrose, sorbitol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted methanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methylcyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-methylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthanecarboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Haarman & Reimer, FEMA 3748, tradename FRESCOLAT® type ML), WS-30, WS-14, Eucalyptus extract (p-Mehtha-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopropyl-bicyclo (2.2.1), Heptane-2-carboxamide; and Menthol methyl ether, and menthyl pyrrolidone carboxylate among others. These and other suitable cooling agents are further described in the following U.S. patents, all of which are incorporated in their entirety by reference hereto: U.S. Pat. Nos. 4,230,688; 4,032,661; 4,459,425; 4,136,163; 5,266,592; 6,627,233. In some embodiments, warming components may be selected from a wide variety of compounds known to provide the sensory signal of warming to the user. These compounds offer the perceived sensation of warmth, particularly in the oral cavity, and often enhance the perception of flavors, sweeteners and other organoleptic components. In some embodiments, useful warming compounds can include vanillyl alcohol n-butylether (TK-1000) supplied by Takasago Perfumary Company Limited, Tokyo, Japan, vanillyl alcohol n-propylether, vanillyl alcohol isopropylether, vanillyl alcohol isobutylether, vanillyl alcohol n-aminoether, vanillyl alcohol isoamyleather, vanillyl alcohol n-hexyleather, vanillyl alcohol methylether, vanillyl alcohol ethylether, gingerol, shogaol, paradol, zingerone, capsaicin, dihydrocapsaicin, nordihydrocapsaicin, homocapsaicin, homodihydrocapsaicin, ethanol, isopropyl alcohol, iso-amylalcohol, benzyl alcohol, glycerine, and combinations thereof.

In some embodiments, a tingling sensation can be provided. One such tingling sensation is provided by adding jambu, oleoresin, or spilanthol to some examples. In some embodiments, alkylamides extracted from materials such as jambu or sanshool can be included. Additionally, in some embodiments, a sensation is created due to effervescence. Such effervescence is created by combining an alkaline material with an acidic material. In some embodiments, an alkaline material can include alkali metal carbonates, alkali metal bicarbonates, alkaline earth metal carbonates, alkaline earth metal bicarbonates and mixtures thereof. In some embodiments, an acidic material can include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof. Examples of "tingling" type sensates can be found in U.S. Pat. No. 6,780,443, the entire contents of which are incorporated herein by reference for all purposes.

Sensate components may also be referred to as "trigeminal stimulants" such as those disclosed in U.S. Patent Application No. 2005/0202118, which is incorporated herein by reference. Trigeminal stimulants are defined as an orally consumed product or agent that stimulates the trigeminal nerve. Examples of cooling agents which are trigeminal stimulants include menthol, WS-3, N-substituted p-menthane carboxamide, acyclic carboxamides including WS-23, methyl succinate, menthane glycerol ketals, bulk sweeteners such as xylitol, erythritol, dextrose, and sorbitol, and combinations thereof. Trigeminal stimulants can also include flavors, tingling agents, Jambu extract, vanillyl alkyl ethers, such as vanillyl n-butyl ether, spilanthol, Echinacea extract, Northern Prickly Ash extract, capsaicin, *capsicum* oleoresin, red pepper oleoresin, black pepper oleoresin, piperine, ginger oleoresin, gingerol, shoagol, cinnamon oleoresin, *cassia* oleoresin, cinnamic aldehyde, eugenol, cyclic acetal of vanillin and menthol glycerin ether, unsaturated amides, and combinations thereof.

Breath fresheners can include essential oils as well as various aldehydes, alcohols, and similar materials. In some embodiments, essential oils can include oils of spearmint, peppermint, wintergreen, sassafras, chlorophyll, citral, geraniol, cardamom, clove, sage, carvacrol, eucalyptus, cardamom, magnolia bark extract, marjoram, cinnamon, lemon, lime, grapefruit, and orange. In some embodiments, aldehydes such as cinnamic aldehyde and salicylaldehyde can be used. Additionally, chemicals such as menthol, carvone, isogarrigol, and anethole can function as breath fresheners. Of these, the most commonly employed are oils of peppermint, spearmint and chlorophyll.

In addition to essential oils and chemicals derived from them, some embodiments breath fresheners can include but are not limited to zinc citrate, zinc acetate, zinc fluoride, zinc ammonium sulfate, zinc bromide, zinc iodide, zinc chloride, zinc nitrate, zinc fluorosilicate, zinc gluconate, zinc tartarate, zinc succinate, zinc formate, zinc chromate, zinc phenol sulfonate, zinc dithionate, zinc sulfate, silver nitrate, zinc salicylate, zinc glycerophosphate, copper nitrate, chlorophyll, copper chlorophyll, chlorophyllin, hydrogenated cottonseed oil, chlorine dioxide, beta cyclodextrin, zeolite, silica-based materials, carbon-based materials, enzymes such as laccase, and combinations thereof. In some embodiments, the release profiles of probiotics can be managed for, but not limited to, lactic acid producing microorganisms such as *Bacillus coagulans, Bacillus subtilis, Bacillus laterosporus, Bacillus laevolacticus, Sporolactobacillus inulinus, Lactobacillus acidophilus, Lactobacillus curvatus, Lactobacillus plantarum, Lactobacillus jenseni, Lactobacillus casei, Lactobacillus fermentum, Lactococcus lactis, Pedioccocus acidilacti, Pedioccocus pentosaceus, Pedioccocus urinae, Leuconostoc mesenteroides, Bacillus coagulans; Bacillus subtilis, Bacillus laterosporus, Bacillus laevolacticus, Sporolactobacillus inulinus* and mixtures thereof. Breath fresheners are also known by the following trade names: Retsyn™, Actizol™, and Nutrazin™. Examples of malodor-controlling compositions are also included in U.S. Pat. No. 5,300,305 to Stapler et al. and in U.S. Patent Application Publication Nos. 2003/0215417 and 2004/0081713 which are incorporated in their entirety herein by reference for all purposes.

Dental care ingredients (also known as oral care ingredients) may include but are not limited to tooth whiteners, stain removers, oral cleaning, bleaching agents, desensitizing agents, dental remineralization agents, antibacterial agents, anticaries agents, plaque acid buffering agents, surfactants and anticalculus agents. Non-limiting examples of such ingredients can include, hydrolytic agents including proteolytic enzymes, abrasives such as hydrated silica, calcium carbonate, sodium bicarbonate and alumina, other active stain-removing components such as surface-active agents, including, but not limited to anionic surfactants such as sodium stearate, sodium palminate, sulfated butyl oleate, sodium oleate, salts of fumaric acid, glycerol, hydroxylated lecithin, sodium lauryl sulfate and chelators such as polyphosphates, which are typically employed as tartar control ingredients. In some embodiments, dental care ingredients can also include tetrasodium pyrophosphate and sodium tripolyphosphate, sodium bicarbonate, sodium acid pyrophosphate, sodium tripolyphosphate, xylitol, sodium hexametaphosphate.

In some embodiments, peroxides such as carbamide peroxide, calcium peroxide, magnesium peroxide, sodium peroxide, hydrogen peroxide, and peroxydiphospate are included. In some embodiments, potassium nitrate and potassium citrate are included. Other examples can include casein glycomacropeptide, calcium casein peptone-calcium phosphate, casein phosphopeptides, casein phosphopeptide-amorphous calcium phosphate (CPP-ACP), and amorphous calcium phosphate. Still other examples can include papaine, krillase, pepsin, trypsin, lysozyme, dextranase, mutanase, glycoamylase, amylase, glucose oxidase, and combinations thereof.

Further examples can include surfactants such as sodium stearate, sodium ricinoleate, and sodium lauryl sulfate surfactants for use in some embodiments to achieve increased prophylactic action and to render the dental care ingredients more cosmetically acceptable. Surfactants can preferably be detersive materials which impart to the composition detersive and foaming properties. Suitable examples of surfactants are water-soluble salts of higher fatty acid monoglyceride rnonosulfates, such as the sodium salt of the monosulfated monoglyceride of hydgrogenated coconut oil fatty acids, higher alkyl sulfates such as sodium lauryl sulfate, alkyl aryl sulfonates such as sodium dodecyl benzene sulfonate, higher alkyl sulfoacetates, sodium lauryl sulfoacetate, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine.

In addition to surfactants, dental care ingredients can include antibacterial agents such as, but not limited to, triclosan, chlorhexidine, zinc citrate, silver nitrate, copper, limonene, and cetyl pyridinium chloride. In some embodiments, additional anticaries agents can include fluoride ions or fluorine-providing components such as inorganic fluoride salts. In some embodiments, soluble alkali metal salts, for example, sodium fluoride, potassium fluoride, sodium fluorosilicate, ammonium fluorosilicate, sodium monofluorophosphate, as well as tin fluorides, such as stannous fluoride and stannous chloride can be included. In some embodiments, a fluorine-containing compound having a beneficial effect on the care and hygiene of the oral cavity, e.g., diminution of enamel solubility in acid and protection of the teeth against decay may also be included as an ingredient. Examples thereof include sodium fluoride, stannous fluoride, potassium fluoride, potassium stannous fluoride (SnF.sub.2-KF), sodium hexafluorostannate, stannous chlorofluoride, sodium fluorozirconate, and sodium monofluorophosphate. In some embodiments, urea is included.

Further examples are included in the following U.S. patents and U.S. published patent applications, the contents of all of which are incorporated in their entirety herein by reference for all purposes: U.S. Pat. No. 5,227,154 to Reynolds, U.S. Pat. No. 5,378,131 to Greenberg, U.S. Pat. No. 6,846,500 to Luo et al., U.S. Pat. No. 6,733,818 to Luo et al., U.S. Pat. No. 6,696,044 to Luo et al., U.S. Pat. No. 6,685,916 to Holme et al., U.S. Pat. No. 6,485,739 to Luo et al., U.S. Pat. No. 6,479,071 to Holme et al., U.S. Pat. No. 6,471,945 to Luo et al., U.S. Patent Publication Nos. 20050025721 to Holme et al., 2005008732 to Gebreselassie et al., and 20040136928 to Holme et al.

Throat soothing ingredients can include analgesics, anesthetics, demulcents, antiseptic, and combinations thereof. In some embodiments, analgesics/anesthetics can include menthol, phenol, hexylresorcinol, benzocaine, dyclonine hydrochloride, benzyl alcohol, salicyl alcohol, and combinations thereof. In some embodiments, demulcents can include but are not limited to slippery elm bark, pectin, gelatin, and combinations thereof. In some embodiments, antiseptic ingredients can include cetylpyridinium chloride, domiphen bromide, dequalinium chloride, and combinations thereof.

In some embodiments, antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof can be included.

In some embodiments, throat soothing agents such as honey, propolis, aloe vera, glycerine, menthol and combinations thereof can be included. In still other embodiments, cough suppressants can be included. Such cough suppressants can fall into two groups: those that alter the consistency or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, antitussives can include, but are not limited to, the group consisting of codeine, dextromethorphan, dextrorphan, diphenhydramine, hydrocodone, noscapine, oxycodone, pentoxyverine and combinations thereof. In some embodiments, antihistamines can include, but are not limited to, acrivastine, azatadine, brompheniramine, chlorpheniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, non-sedating antihistamines can include, but are not limited to, astemizole, cetirizine, ebastine, fexofenadine, loratidine, terfenadine, and combinations thereof.

In some embodiments, expectorants can include, but are not limited to, ammonium chloride, guaifenesin, ipecac fluid extract, potassium iodide and combinations thereof. In some embodiments, mucolytics can include, but are not limited to, acetylcycsteine, ambroxol, bromhexine and combinations thereof. In some embodiments, analgesic, antipyretic and anti-inflammatory agents can include, but are not limited to, acetaminophen, aspirin, diclofenac, diflunisal, etodolac, fenoprofen, flurbiprofen, ibuprofen, ketoprofen, ketorolac, nabumetone, naproxen, piroxicam, caffeine, paracetamol and mixtures thereof. In some embodiments, local anesthetics can include, but are not limited to, lidocaine, benzocaine, phenol, dyclonine, benzonotate and mixtures thereof.

In some embodiments nasal decongestants and ingredients that provide the perception of nasal clearing can be included. In some embodiments, nasal decongestants can include but are not limited to phenylpropanolamine, pseudoephedrine, ephedrine, phenylephrine, oxymetazoline, and combinations thereof. In some embodiments ingredients that provide a perception of nasal clearing can include but are not limited to menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, gums, flowers and other botanicals, resins, animal secretions, and synthetic aromatic materials.

In some embodiments, one or more colors can be included. As classified by the United States Food, Drug, and Cosmetic Act (21 C.F.R. 73), colors can include exempt from certification colors (sometimes referred to as natural even though they can be synthetically manufactured) and certified colors (sometimes referred to as artificial), or combinations thereof. In some embodiments, exempt from certification or natural colors can include, but are not limited to annatto extract, (E160b), bixin, norbixin, astaxanthin, dehydrated beets (beet powder), beetroot red/betanin (E162), ultramarine blue, canthaxanthin (E161g), cryptoxanthin (E161c), rubixanthin (E161d), violanxanthin (E161e), rhodoxanthin (E161f), caramel (E150(a-d)), [beta]-apo-8'-carotenal (E160e), [beta]-carotene (E160a), alpha carotene, gamma carotene, ethyl ester of beta-apo-8 carotenal (E160f), flavoxanthin (E161a), lutein (E161b), cochineal extract (E120); carmine (E132), carmoisine/azorubine (E122), sodium copper chlorophyllin (E141), chlorophyll (E140), toasted partially defatted cooked cottonseed flour, ferrous gluconate, ferrous lactate, grape color extract, grape skin extract (enocianina), anthocyanins (E163), haeniatococcus algae meal, synthetic iron oxide, iron oxides and hydroxides (E172), fruit juice, vegetable juice, dried algae meal, tagetes (Aztec marigold) meal and extract, carrot oil, corn endosperm oil, paprika, paprika oleoresin, phaffia yeast, riboflavin (E101), saffron, titanium dioxide, turmeric (E100), turmeric oleoresin, amaranth (E123), capsanthinkapsorbin (E160c), lycopene (E160d), and combinations thereof.

In some embodiments, certified colors can include, but are not limited to, FD&C blue #1, FD&C blue #2, FD&C green #3, FD&C red #3, FD&C red #40, FD&C yellow #5 and FD&C yellow #6, tartrazine (E102), quinoline yellow (E104), sunset yellow (E110), ponceau (E124), erythrosine (E127), patent blue V (E131), titanium dioxide (E171), aluminium (E173), silver (E174), gold (E175), pigment rubine/lithol rubine BK (E180), calcium carbonate (E170), carbon black (E153), black PN/brilliant black BN (E151), green S/acid brilliant green BS (E142), and combinations thereof. In some embodiments, certified colors can include FD&C aluminum lakes. These consist of the aluminum salts of FD&C dyes extended on an insoluble substrate of alumina hydrate. Additionally, in some embodiments, certified colors can be included as calcium salts.

Mouth moisteners can include, but are not limited to, saliva stimulators such as acids and salts and combinations thereof. In some embodiments, acids can include acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof.

Mouth moisteners can also include hydrocolloid materials that hydrate and may adhere to oral surface to provide a sensation of mouth moistening. Hydrocolloid materials can include naturally occurring materials such as plant exudates, seed gums, and seaweed extracts or they can be chemically modified materials such as cellulose, starch, or natural gum derivatives. In some embodiments, hydrocolloid materials can include pectin, gum arabic, acacia gum, alginates, agar, carageenans, guar gum, xanthan gum, locust bean gum, gelatin, gellan gum, galactomannans, tragacanth gum, karaya gum, curdlan, konjac, chitosan, xyloglucan, beta glucan, furcellaran, gum ghatti, tamarin, bacterial gums, and combinations thereof. Additionally, in some embodiments, modified natural gums such as propylene glycol alginate, carboxymethyl locust bean gum, low methoxyl pectin, and their combinations can be included. In some embodiments, modified celluloses can be included such as microcrystalline cellulose, carboxymethlcellulose (CMC), methylcellulose (MC), hydroxypropylmethylcellulose (HPCM), and hydroxypropylcellulose (MPC), and combinations thereof.

Similarly, humectants which can provide a perception of mouth hydration can be included. Such humectants can include, but are not limited to glycerol, sorbitol, polyethylene glycol, erythritol, and xylitol. Additionally, in some embodiments, fats can provide a perception of mouth moistening. Such fats can include medium chain triglycerides, vegetable oils, fish oils, mineral oils, and combinations thereof.

Food acids can include, but are not limited to acetic acid, adipic acid, ascorbic acid, butyric acid, citric acid, formic acid, fumaric acid, glyconic acid, lactic acid, phosphoric acid, malic acid, oxalic acid, succinic acid, tartaric acid and combinations thereof.

Micronutrients can include materials that have an impact on the nutritional well being of an organism even though the quantity required by the organism to have the desired effect is small relative to macronutrients such as protein, carbohydrate, and fat. Micronutrients can include, but are not limited to vitamins, minerals, enzymes, phytochemicals, antioxidants, and combinations thereof.

In some embodiments, vitamins can include fat soluble vitamins such as vitamin A, vitamin D, vitamin E, and vitamin K and combinations thereof. In some embodiments, vitamins can include water soluble vitamins such as vitamin C (ascorbic acid), the B vitamins (thiamine or B1, riboflavoin or B2, niacin or B3, pyridoxine or B6, folic acid or B9, cyanocobalimin or B12, pantothenic acid, biotin), and combinations thereof. Fats may comprise nutritional oils, including various fish oils (such as cod liver oil) and constituents compounds thereof.

In some embodiments minerals can include but are not limited to sodium, magnesium, chromium, iodine, iron, manganese, calcium, copper, fluoride, potassium, phosphorous, molybdenum, selenium, zinc, and combinations thereof.

In some embodiments micronutrients can include but are not limited to L-carnitine, choline, coenzyme Q10, alpha-lipoic acid, omega-3-fatty acids, pepsin, phytase, trypsin, lipases, proteases, cellulases, and combinations thereof.

Antioxidants can include materials that scavenge free radicals. In some embodiments, antioxidants can include but are not limited to ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments phytochemicals can include but are not limited to cartotenoids, chlorophyll, chlorophyllin, fiber, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

An effervescent system may include one or more edible acids and one or more edible alkaline materials. The edible acid(s) and the edible alkaline material(s) may react together to generate effervescence.

In some embodiments, the alkaline material(s) may be selected from, but is not limited to, alkali metal carbonates, alkali metal bicarbonates, alkaline earth metal carbonates, alkaline earth metal bicarbonates, and combinations thereof. The edible acid(s) may be selected from, but is not limited to, citric acid, phosphoric acid, tartaric acid, malic acid, ascorbic acid, and combinations thereof. In some embodiments, an effervescing system may include one or more other ingredients such as, for example, carbon dioxide, oral care ingredients, flavorants, etc.

For examples of use of an effervescing system, reference is made to U.S. Provisional Patent No. 60/618,222 filed Oct. 13, 2004, and entitled "Effervescent Pressed Gum Tablet Compositions," the contents of which are incorporated herein by reference for all purposes. Other examples can be found in U.S. Pat. No. 6,235,318, the contents of which are incorporated herein by reference for all purposes.

In some embodiments, nutraceuticals or nutritional supplements, such as any of those disclosed in U.S. Pat. No. 6,949,264, which is incorporated by reference herein, can be included. In some embodiments, traditional Chinese medicines or extracts thereof, such as any of those described in International Publication No. WO2008045579, which is incorporated by reference herein, can be included.

In some embodiments, herbs and spices can be included as active components, for example, to promote health and well being.

In some embodiments, alginates, such as sodium alginate, can be included for indigestion relief. Alginates can react with acids contained in products, which can reduce the shelf life of the product. Alginates also can pose manufacturing problems because they are hydrocolloids and tend to hold moisture and gel when manufactured in accordance with conventional confectionery manufacturing techniques. This makes it difficult to include alginates in confectionery compositions, particularly hard candy compositions, which require hard boiling to boil off moisture during the manufacturing process. By incorporating alginates into the capillaries of the confectionery product as described herein, it is anticipated that these problems can be alleviated. In particular, alginates can be separated from any acid components by including acids in a different region, such as the extruded body portion, a coating region or a separate group of capillaries. The adverse effects of the acids on the alginates may thus be reduced. Further, by incorporating alginates into the confectionery product via the capillaries rather than the confectionery composition of the extruded body portion, the manufacturing difficulties discussed above may be alleviated. The confectionery composition that will be used to form the extruded body portion can be processed according to conventional techniques, including hard boiling to boil off moisture. The alginate-containing fill material subsequently can be filled into the capillaries during or after extrusion.

In another embodiment of the present invention, two or more reactive components can be included in the confectionery product. It may be desirable to incorporate the reactive components into separate and distinct regions of the product. For example, the reactive components may be separated between the extruded body portion and the capillaries or two different groups of capillaries. The reactive components may then react with one another when the confectionery product is consumed. In some embodiments, each respective region is free of the opposing reactive component.

Reactive components can include calcium and phosphate ions. Calcium and phosphate ions are reactable when they combine to form calcium phosphate which may then remineralize a tooth surface. Sources for calcium ions can include, but are not limited to, calcium gluconate, calcium iactate gluconate, calcium-boro gluconate, calcium citrate, calcium ascorbate, calcium lactobionate, calcium brornolactobionate, calcium malate citrate, calcium orotate, calcium pyruvate, calcium lactate, calcium carbonate, tricalcium phosphate, tricalcium citrate, calcium fumarate, calcium lactate pentahydrate, calcium chloride, calcium sulfate, calcium glutareate, calcium hydroxide, calcium oxide, and combinations thereof.

Sources for phosphate ions can include, but are not limited to, phosphoric acid, calcium phosphate (mono-, di-, and tri-basic), sodium phosphate (mono-, di-, and tri-basic), disodium diphosphate, tetrasodium diphosphate, pentapotassium triphosphate, pentasodium triphosphate, sodium polyphosphate (Graham's salt), sodium hexametaphosphate, sodium potassium polyphosphate (Tammann's salt), Kurrol's salt $(KPO_3)_n$, sodium tripolyphosphate, disodium phosphate, magnesium phosphate (mono-, di-, and tri-basic), potassium phosphate (mono-, di-, and tri-basic), bone phosphate, ammonium phosphate, dibasic, ammonium polyphosphate, calcium polyphosphate, calcium pyrophosphate, potassium polyphosphate, potassium pyrophosphate, and combinations thereof.

In some embodiments, the calcium ion and phosphate ion sources are selected with similar release rates so that the remineralization reaction between the ions will occur on the tooth surface.

In some embodiments, the reactive components can include ingredients with pH below 7.0 and ingredients with pH above 7.0. Ingredients with pH above 7.0 can be characterized as being alkaline while ingredients with pH below 7.0 can be characterized as acidic. Ingredients with pH above 7.0 can include, but are not limited to, tripotassium phosphate, dipotassium phosphate, sodium bicarbonate, calcium hydroxide, sodium hydroxide, calcium fluoride, calcium phosphate, calcium sulphate, potassium chloride, potassium phosphate, calcium carbonate, activated carbon, alum, aluminum hydroxide, aluminum potassium sulfate, aluminum sodium sulfate, ammonium carbonate, ammonium bicarbonate, ammonium chloride, ammonium hydroxide, ammonium citrate, ammonium gluconate, ammonium sulfate, ammonium sulfite, ammonium sulfide, ammonium phosphate, calcium gluconate, calcium glycerophosphate, calcium hexametaphosphate, calcium peroxide, calcium hypophosphite, calcium sulfate, chlorine dioxide, copper gluconate, copper sulfate, ferric chloride, ferric phosphate, ferric pyrophosphate, ferric oxide, ferric sulfate, ferric sodium pyrophosphate, ferrous carbonate, ferrous gluconate, ferrous sulfate, hydrogen peroxide, magnesium carbonate, magnesium chloride, magnesium gluconate, magnesium glycerophosphate, magnesium hydroxide, magnesium phosphate, magnesium sulfate, manganese glycerophosphate, manganese hypophosphite, manganese sulfate, potassium carbonate, potassium bicarbonate, potassium chloride, potassium gluconate, potassium hydroxide, potassium glycerophosphate, potassium tripolyphosphate, sodium carbonate, sodium chloride, sodium hexametaphosphate, sodium hydroxide, sodium fluoride, sodium hypophosphite, sodium metaphosphate, sodium phosphate, sodium pyrophosphate, sodium sulfate, sodium sulfide, sodium sulfite, sodium tripolyphosphate, stannous chloride, stannic chlorite, zinc carbonate, zinc chloride, zinc oxide, zinc gluconate, sodium chlorite, and combinations thereof.

Ingredients with pH below 7.0 can include, but are not limited to, acetic acid, adipic acid, ascorbic acid, butyric acid, citric acid, formic acid, fumaric acid, glyconic acid, lactic acid, phosphoric acid, malic acid, oxalic acid, succinic acid, tartaric acid, glucono-delta-iactone and combinations thereof.

In some embodiments, the ingredients with pH below 7.0 and the ingredients with pH above 7 0 are selected with similar release rates so that the neutralization reaction will occur in the mouth.

In some embodiments, the reactive components can include peroxy compounds and ingredients with pH above 7.0. Suitable peroxy compounds can include, but are not limited to, any orally acceptable compound(s) that delivers perhydroxy ($OOH^-$) ions, such as hydrogen peroxide, peroxides of alkali and alkaline earth metals, organic peroxy compounds, and peroxy acids and salts thereof. Peroxides of alkali and alkaline earth metals can include, but are not limited to, lithium peroxide, potassium peroxide, sodium peroxide, magnesium peroxide, calcium peroxide, and barium peroxide. Organic peroxy compounds can include, but are not limited to, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and the like. Peroxy acids and their salts can include, but are not limited to, organic peroxy acids such as alkyl peroxy acids and monoperoxyphthalate, as well as inorganic peroxy acid salts including persulfate, dipersulfate, nercarbonate, perphosphate, perborate and persilicate salts of alkali and alkaline earth metals such as lithium, potassium, sodium, magnesium, calcium and barium. Another useful peroxy compound is sodium pyrophosphate peroxyhydrate. Suitable ingredients with pH above 7.0 are listed above.

In some embodiments, the peroxy compounds and the ingredients with pH above 7.0 are selected with similar release rates so that the whitening or teeth cleaning reaction will occur in the mouth.

In some embodiments, the reactive components can include ingredients with pH above 7.0 and ingredients with pH below 7.0 that react to effervesce when consumed. Suitable ingredients with pH above 7.0 can include, but are not limited to, any orally acceptable bicarbonate such as alkali metal bicarbonates such as sodium and potassium bicarbonates, ammonium bicarbonate and the like. As discussed above, ingredients with pH below 7.0 can include, but are not limited to acetic acid, adipic acid, ascorbic acid, butyric acid, citric acid, formic acid, fumaric acid, glyconic acid, lactic acid, phosphoric acid, malic acid, oxalic acid, succinic acid, tartaric acid, glucono-delta-lactone, and combinations thereof.

In some embodiments, the ingredients with pH above 7.0 and ingredients with pH below 7.0 that react to effervesce are selected with similar release rates so that the effervescence reaction will occur in the mouth.

In some embodiments, ingredients providing a sensation to the consumer of the confectionery product are included to indicate that the reaction is proceeding. In some embodiments, the sensation is cooling, warming, effervescence, tingling, or salivation. A variety of well known cooling agents, warming agents, effervescent agents or tingling agents may be employed, such as any of those described herein.

In some embodiments where the reactive components are included in separate regions of the confectionery product, the components that provide a sensation are included in one region. In some embodiments, the components that provide a sensation are included in both regions of the confectionery product. In some embodiments, the components that provide a sensation will provide the same sensation while in other embodiments, the sensation will be different. In some embodiments, the components that provide a sensation have similar release rates as compared to the release rates of the components that react so that the reaction proceeds at the same time the sensation is provided in the mouth.

In some embodiments, the reactive components can include chelating agents and acids. Chelating agents are tooth whitening agents suitable for use in some embodiments of the present invention. Chelators are capable of strongly binding with metal ions, such as calcium. For example, chelating agents are able to complex calcium found in the cell walls of bacteria, a major component of plaque. Chelating agents can also disrupt plaque by removing calcium from the calcium bridges, which help hold the plaque matrix together. Examples of suitable chelators include phosphate salts. In some embodiments, the phosphate salt is selected from one of the following: pyrophosphates, triphosphates, polyphosphates, polyphosphonates and combinations thereof. Polyphosphates, such as sodium tripolyphosphate (STP) and sodium hexametaphosphate (SHMP), which are commonly employed in tooth whitening chewing gum products, react with acids (e.g., citric acid). This reduces the shelf life of the product and results in the production of undesirable by-products. By separating the polyphosphate active and acid components into different regions of the product, such as, for instance, the body portion and the capillaries or different groups of capillaries, the adverse effects of the acid on the polyphosphate may be reduced.

In some embodiments, the reactive components can include hydrolytic agents, which react with a variety of components typically included in confectionery products, including flavors, peroxides, fluorides and water. Hydrolytic agents are used as tooth whitening agents. Hydrolytic agents function to whiten teeth by removing the plaque and calculus that entrap the stain. Examples of hydrolytic agents which may be employed in the confectionery product include, but are not limited to, proteolytic enzymes (e.g., papaine), lipase, amylase and glucoamylase. Such hydrolytic agents react unfavorably with the following components: flavors, peroxides, fluorides and water. By separating hydrolytic agents from these components in different regions of the product, such as, for instance, the body portion and the capillaries or different groups of capillaries, the adverse effects of such components on the hydrolytic agent may be reduced.

In some embodiments, the reactive components can include oxidizing agents, such as peroxides, which react with flavors and aldehydes. Peroxides are used as tooth whitening agents, which are believed to whiten teeth by releasing hydroxyl radicals capable of breaking down the plaque-stain complex into a form that can be flushed away or removed by abrasives. Separating peroxides into different regions of the product from flavors and aldehydes may prevent the peroxides from interacting therewith.

In some embodiments, the reactive components can include surfactants, such as anionic surfactants, which can react with lecithin and acids. Certain fatty acid salts interact with lecithin, which is often used in gums and other food products to help different parts mix together well. Moreover, fatty acid salts can undergo changes in acidic formulations, such as fruit gums. By separating surfactants from such components in different regions of the confectionery product, these adverse interactions may be substantially reduced.

In some embodiments, the reactive components can include intense sweeteners, such as Neotame and Aspartame, which can interact with flavors, aldehydes and glycerine. Incorporating intense sweeteners into different regions of the confectionery product may prevent these actives from physically interacting with flavors, aldehydes or glycerin which are often present in such products.

If desired, the fill material may additionally comprise particulate material. The particulate material may be used for a number of purposes, such as sensory agents to provide a "crunch" when the product is being chewed, or to provide an abrasive agent to help clean/whiten teeth.

Examples of abrasive agents include silicas, aluminas, phosphates, carbonates and combinations thereof. In some embodiments, the abrasive agent is a silica selected from: precipitated silica, silica gels and combinations thereof. Moreover, in some embodiments the abrasive agent is selected from the following: calcium carbonate, sodium bicarbonate, sodium metaphosphate, potassium metaphosphate, tricalcium phosphate, dehydrated dicalcium phosphate and combinations thereof. The abrasive polishing material contemplated for use in the compositions of the present invention can be any material which does not excessively abrade dentin.

In some embodiments, the product may include two or more different active/reactive components that work together to create a complementary or intensity-building effect. This may provide an enhanced overall product experience upon consumption, for example, by imparting an extended and/or more intense product profile. In particular, the two or more active/reactive components may be distinct from and complementary to one another. In some embodiments, two different active/reactive components that are complementary, such as two different cooling agents, could be incorporated into different regions of the product. The different regions may include, for instance, the body portion, different capillaries or groups of capillaries, an optional center-fill region, an optional coating region, and the like. The complementary active/reactive components may be incorporated into certain regions of the product to create the desired product profile. For instance, an active that exhibits an intense up-front burst of its attribute, such as cooling, may be incorporated into a coating region and a complementary active that exhibits a milder and longer duration of its attribute, such as a milder cooling sensation, may be incorporated into the capillaries. This could create a product with a cooling profile that initiates with a high intensity and extends into a milder cooling sensation over a longer period of time than if individual cooling agents had been used alone.

In some embodiments, the two different active/reactive components may have different mechanisms of action, yet may complement one another. For example, an active/reactive component having a mechanical mechanism of action could be incorporated into the coating region or an outer group of capillaries disposed in the body portion. A complementary active/reactive component having a chemical mechanism of action could be incorporated into an inner group of capillaries disposed in the body portion. Upon consumption, the two complementary active/reactive components may impart a product profile that is higher in intensity and/or longer in duration.

In another embodiment of the present invention, there is provided a confectionery product including an extruded body portion, the body portion having a plurality of capillaries disposed therein, and including a first sensate and a second sensate which is different from the first sensate located in separate and discrete regions of the product and being adapted to provide sequential release profiles. The separate and distinct regions of the product can include a variety of different product regions. For instance, the regions of the product include the extruded body portion, the capillaries, different groups of capillaries, an optional center-fill region, an optional coating region, and the like. In some embodiments, the separate and discrete regions can include the body portion and the capillaries or two different groups of capillaries. In some embodiments, the region including the first sensate is essentially free of the second sensate and the region including the second sensate is essentially free of the first sensate.

For example, the first sensate may be a warming agent and the second sensate may be a cooling agent or vice-versa. The region including the warming agent may be essentially free of cooling agents and the region including the cooling agent may be essentially free of warming agents.

In some embodiments, the first sensate is distinct from and complementary to the second sensate. For instance, two distinct warming agents, may be employed having different mechanisms of action. The distinct warming agents, however, may be complementary to one another. They may enhance the intensity and/or duration of the warming profile.

In some embodiments, the first sensate and the second sensate have different mechanisms of action. The first sensate may have a chemical mechanism of action, such as, for instance, a trigeminal stimulant, and the second sensate may have a thermal mechanism of action, such as, for instance, an endothermic agent or an exothermic agent.

Exemplary endothermic agents include polyols having a negative heat of solution, including, but not limited to, xylitol, erythritol and sorbitol. These agents can impart a cooling sensation upon consumption.

Exemplary exothermic agents include supersaturated solutions that use crystallization enthalpy to impart a warming sensation. Supersaturated solutions can be formed by heating aqueous solutions to a temperature of suitably from about 30° C. (86° F.) to about 100° C. (212° F.), and more suitably, from about 32° C. (90° F.) to about 90° C. (194° F.), and dissolving particles (e.g., salts or sugars) in the heated aqueous solutions. Typically, the aqueous solutions are made up of water. Under these heated conditions, more particles are capable of dissolving in the solutions, thereby producing supersaturated solutions. These supersaturated solutions are unstable and will completely crystallize if exposed to an activation means such as a nucleation site (e.g., a seed crystal). As the solute from the supersaturated solution crystallizes, heat is produced through crystallization enthalpy or latent heat of fusion.

Suitable supersaturated solutions, therefore, are capable of producing a high crystallization enthalpy and a high crystallization rate. Generally, the supersaturated solutions are capable of generating a crystallization enthalpy of at least about 70 Joules/gram, and more suitably at least about 125 Joules/gram. In some embodiments, the supersaturated solutions may be capable of generating a crystallization enthalpy of from about 70 Joules/gram to about 500 Joules/gram. Additionally, the supersaturated solutions may produce a crystallized solid product having a crystallization rate, that is the rate at which the solution crystallizes, of at least about 0.01 centimeters/second, more suitably at least about 0.03 centimeters/second, even more suitably, at least about 0.05 centimeters/second, and even more suitably at least about 0.10 centimeters/second.

Suitable supersaturated solutions may include, for example, supersaturated solutions prepared from aqueous solutions of polyols, such as xylitol, erythritol, sorbitol or combinations thereof.

In some embodiments, the confectionery product also includes one or more activation means to initiate crystallization of the supersaturated solution. The activation means may be one or more seed crystals having a similar chemistry as compared to the supersaturated solution. More particularly, a suitable activation means may have crystallographic data being within about 15% of that of the material to be crystallized in the supersaturated solution. For instance, if the supersaturated solution is a supersaturated xylitol solution, the activation means is suitably one or more xylitol seed crystals. The activation means may be present in the composition in an amount of from about 0.1% (by weight) to about 80% (by weight). The activation means utilized in the composition generally has a particle size of from about 0.01 micrometers to about 500 micrometers, desirably from about 1 micrometers to about 100 micrometers, desirably from about 5 micrometers to about 50 micrometers, and more desirably from about 10 micrometers to about 30 micrometers to facilitate substantial and continuous crystallization of the supersaturated solution.

For example, in accordance with one embodiment, the activation means, such as one or more seed crystals, are included in the extruded body portion of the confectionery product and the supersaturated solution, such as a supersaturated solution prepared from an aqueous polyol solution, is included in a liquid fill material contained in the capillaries. Upon consumption, the seed crystals will be released from the body portion and will activate crystallization of the supersaturated polyol solution as it is released from the capillaries. As the polyol in the supersaturated solution crystallizes, heat is produced, thereby imparting a warming sensation during consumption.

In some embodiments, a cooling agent may be included in another region of the product, other than the capillaries containing the supersaturated solution. For instance, a cooling agent may be included in the body portion or an optional coating region of the product. This will impart an initial cooling sensation upon consumption of the product. The cooling sensation will shift to a warming sensation due to the heat produced by crystallization of the solute from the supersaturated solution.

In another embodiment of the present invention, the body portion includes the first sensate and the capillaries are at least partially filled with a fill material including the second sensate.

In another embodiment, a first group of capillaries is distributed around the periphery of the body portion and a second group of capillaries is distributed interior to the first group. The first group of capillaries may be at least partially filled with a first fill material including the first sensate and the second group of capillaries may be at least partially filled with a second fill material including the second sensate. The first and second groups of capillaries may have the same or different diameters. The two groups of capillaries also may have the same or different cross-sectional profiles. For instance, the first, or outer, group of capillaries may have a larger diameter than the second, or interiorly located, group of capillaries. A larger amount of fill material accordingly can be included in the first, or outer, group of capillaries. This can enable incorporation of a higher amount of the first sensate into the overall product, which can be used to impart a more intense sensation of the first sensate with a milder sensation of the second sensate. This could be desirable, for example, to impart varying sensation profiles. For instance, a product could be provided having an intense, initial cooling sensation due to a first cooling agent and then an extended, but milder cooling sensation due to a second cooling agent contained in the inner, smaller diameter capillaries.

In yet another embodiment; the confectionery product includes a center-fill region. The plurality of capillaries is distributed around the periphery of the body portion and surrounding the center-fill region. The center-fill region includes a first fill material including the first sensate and the capillaries are at least partially filled with a second fill material including the second sensate. The fill material in the center-fill region may be liquid, semi-solid, solid or combinations thereof. For instance, the center-fill region may contain a liquid-fill composition. In some embodiments, the center-fill region may be a chewing gum composition. For instance, the extruded body portion may be a hard candy composition containing a plurality of capillaries distributed around a center-fill chewing gum region.

In another embodiment, the confectionery product includes a coating region enveloping the extruded body portion. The coating region may partially or fully envelop the extruded body portion. In some embodiments, the coating region may include the first sensate and the capillaries may be at least partially filled with a fill material including the second sensate.

In some embodiments, the extruded body portion is selected from hard candy, chewy candy, chewing gum and chocolate.

In a further embodiment, there is provided a confectionery product including an extruded body portion, the body portion having a plurality of capillaries disposed therein, one or more of the capillaries being at least partially filled with a fill material including an active and/or reactive component that is volatile at temperatures of 35° C. and higher, and wherein the extruded body portion is essentially free of the volatile active and/or reactive component. A "volatile active" may be any active component that is volatile at temperatures of approximately 35° C. and higher. For example, a number of flavour components are volatile at such temperatures.

In another embodiment, there is provided a confectionery product including an extruded body portion, the body portion having a plurality of capillaries disposed therein, one or more of the capillaries being at least partially filled with a fill material including an active and/or reactive component that degrades when subjected to manufacturing conditions including exposure to temperatures of 50° C. and higher, wherein the extruded body portion is essentially free of the degradable active and/or reactive component. A "degradable active" may be any active component which degrades at temperatures of approximately 50° C. and higher. For example, many vitamins, fibers and acids degrade to at least some extent at such temperatures.

It is often difficult to process volatile and degradable actives under conventional confectionery manufacturing techniques because such processes typically require heating at temperatures that are substantially higher than these actives can withstand without undergoing volatilization or degradation. Thus, volatile and degradable actives often are added into the compositions at late stages of the manufacturing process. For instance, flavour oils and acids typically are added in the final stages of mixing. It also may be necessary to incorporate significantly higher amounts of such actives into confectionery compositions to allow for the loss of some amount of the active or its level of activity during processing.

Embodiments of the present invention, however, can enable such actives to be incorporated into the capillaries that are distributed throughout the extruded body portion of the product rather than the body of the product itself. The fill materials contained in the capillaries will not be exposed to as high a heat history as the main body portion of the product. Accordingly, it is anticipated that by incorporating volatile and/or degradable actives into the capillaries of the confectionery product, the problems associated with active volatilization and/or degradation can, at least in part, be alleviated.

In another embodiment of the present invention, there is provided a confectionery product including an extruded body portion, the body portion having a plurality of capillaries disposed therein, wherein a first group of the capillaries is filled with a first fill material having a first viscosity and including a first active and/or reactive component, and a second group of the capillaries is filled with a second fill material having a second viscosity which is lower than the first viscosity and including a second active and/or reactive component which is different from the first active and/or reactive component, the fill materials being adapted to provide sequential release profiles. In particular, the fill material having a higher viscosity will be thicker and will tend to release slower from the capillaries than the fill material having the lower viscosity. The relative viscosities of the fill materials, therefore, can be adapted to provide the desired sequential release profile. For instance, in one embodiment, a first group of capillaries could include a fill material having a higher viscosity and a pharmaceutical active that has a bitter taste. A second group of capillaries could include a fill material having a lower viscosity than the first fill material. The second fill material could include a taste-masking agent. It is anticipated that the second fill material would flow out of the capillaries faster than the higher viscosity fill material, and the taste-masking agent would be released into the oral cavity before the onset of bitter taste associated with the pharmaceutical active. In some embodiments, the first group of the capillaries is essentially free of the second active and/or reactive component and the second group of the capillaries is essentially free of the first active and/or reactive component.

In another embodiment of the present invention, there is provided a confectionery product including an extruded body portion, the body portion having a plurality of capillaries disposed therein, wherein a first group of the capillaries is filled with a first fill material having a first water solubility and including a first active and/or reactive component, and a second group of the capillaries is filled with a second fill material having a second water solubility which is lower than the first water solubility and including a second active and/or reactive component which is different from the first active and/or reactive component, the fill materials being adapted to provide sequential release profiles. In some embodiments, the first group of the capillaries is essentially free of the second active and/or reactive component and the second group of said capillaries is essentially free of the first active and/or reactive component.

In yet another embodiment, there is provided a confectionery product for imparting a perception of satiety. The confectionery product includes an extruded body portion, the body portion having a plurality of capillaries disposed therein, one or more of the capillaries being at least partially filled with a fill material including a satiety agent and wherein two or more different satiety agents are provided in the same or different capillaries, the satiety agents being selected from sweet flavors, savory flavors, green tea extract, caffeine, phenylalanine, fibers, proteins and lipids.

Sweet flavors can include, for instance, but are not limited to, almond, vanilla, apple, banana, cherry, blueberry, strawberry, raspberry, lemon, lime, orange, peach, apricot, kiwi, pineapple, amaretto, caramel, buttermilk, butterscotch, butter rum, chocolate, coconut, and the like and combinations thereof. Savory flavors can include, for instance, but are not limited to, soy sauce, worcestershire, meat, cheese, cream, pepper, watercress, celery, hickory, mesquite, garlic, onion, mushroom, and the like and combinations thereof.

The source of fiber can include, for instance, guar, glucomannan, potato, cellulose, such as methyl cellulose or hemicellulose, psyllium, pectin, oat fiber, sugar beet, lignin or pectins. The source of protein can include, for instance, casein, whey or soy. Lipids can include, for instance, triglyceride oils, long chain fatty acids and the like.

In yet another embodiment of the present invention, there is provided a dental cleaning confectionery product including an extruded body portion, the body portion having a plurality of capillaries disposed therein, and including two or more different dental cleaning agents located in the same or different regions of the product. In some embodiments, the product is a dental cleaning chewing gum in which the extruded body portion is a chewing gum composition.

The two or more different dental cleaning agents may have different mechanisms of action. In some embodiments, a first dental cleaning agent has a chemical mechanism of action and a second dental cleaning agent has a mechanical mechanism of action.

For instance, the first dental cleaning agent may be a stain removing agent. Stain removing agents can include, but are not limited to, medium and long chain fatty acids, organic acids, organic peroxides, perbenzoic acids, anti-bacterial organic compounds, castor oil, sulfated butyl oleate, medium and long chain fatty acid esters, ricinoleic acid and salts, sulfated butyl oleate, medium and long chain fatty acid esters and salts thereof, sodium oleate, salts of fumaric acid, potassium glomate, organic acid esters of mono- and di-glycerides, succistearin, dioctyl sodium sulfosuccinate, glycerol tristearate, lecithin, hydroxylated lecithin, sodium lauryl sulfate, acetylated monoglycerides, succinylated monoglycerides, monoglyceride citrate, ethoxylated mono- and di-glycerides, sorbitan monostearate, calcium stearyl-2-lactylate, sodium stearyl lactylate, lactylated fatty acid esters of glycerol and propylene glycol, glycerol-lactoesters of $C_8$-$C_{24}$ fatty acids, polyglycerol esters of $C_8$-$C_{24}$ fatty acids, propylene glycol alginate, sucrose $C_8$-$C_{24}$ fatty acid esters, diacetyl tartaric or citric or lactic acid esters of mono and diglycerides, and triacetin and combinations thereof.

The second dental cleaning agent may be a foaming agent, effervescing agent, abrasive agent or any combination thereof.

In some embodiments, the dental cleaning agents are located in separate and distinct regions of the product and are adapted to provide sequential release profiles.

In particular, the product may be adapted such that one of the dental cleaning agents is released prior to the other during consumption. For example, it may be beneficial for a chemical cleaning agent to be released first to provide a chemical pre-treatment step. The mechanical cleaning agent, such as a foaming agent, may subsequently be released to clean the teeth via mechanical action or at least impart a perception of teeth cleaning due to the sensorial cue given off by the active in the oral cavity.

In one embodiment, the capillaries include a fill material containing the first dental cleaning agent and the extruded body portion includes the second dental cleaning agent.

In another embodiment, a first group of capillaries contains a first fill material including the first dental cleaning agent and a second group of capillaries contains a second fill material including the second dental cleaning agent.

In yet another embodiment, a coating region enveloping the product includes the first dental cleaning agent and the capillaries contain a fill material including the second dental cleaning agent. Optionally, the extruded body portion contains a third dental cleaning agent.

The fill material contained in the capillaries may further include a taste-masking agent. In particular, a number of dental cleaning agents exhibit undesirable tastes, such as bitterness. Taste-masking agents may be incorporated to mask, or cover, the undesirable tastes so that the confectionery product has a pleasing flavour profile. Taste-masking agents can include, for instance, but are not limited to, flavour enhancers, polymeric coatings, ion-exchange resins, inclusion complex formation within cyclodextrins and other various technologies known by those of ordinary skill in the art.

The material used to produce the body portion may comprise a number of materials commonly use in the production of confectionery—such as candy, gum and chocolate, etc.

In some embodiments, the body portion is chocolate. Suitable chocolate includes dark, milk, white and compound chocolate. In some embodiments, the body portion is chewing gum, bubble gum or gum base. For instance, the body portion may include the gum base and the remaining chewing gum ingredients may be incorporated into the fill material in the capillaries. In other embodiments, the body portion is candy. Suitable candy includes hard candy, chewy candy, gummy candy, jelly candy, toffee, fudge, nougat and the like.

The capillaries may extend along the substantially entire length of the body portion, but may in some embodiment extend no less than 75%, 80%, 90%, 95% or 99% along the length of the body portion (for example, when it is desired to seal the ends of the body portion). If the capillaries extend along the entire length of body portion, suitably the ends of the capillaries are visible at one or more ends of the body portion.

In some embodiments, the capillaries may remain unfilled, or partially or completely air-filled. In some other embodiments, one or more of the capillaries may be filled with a material which is different from that of the material used to form the body portion. Some embodiments may include a group of capillaries that are unfilled, or air-filled, and another group of capillaries that are at least partially filled with a fill material. Different capillaries may incorporate different materials if desired. The capillaries may be at least partially filled with a fluid or other material. Such a fluid may be a liquid. The capillaries may be filled with a material which is solid at a room temperature and fluid at a temperature greater than room temperature. For example, a molten chocolate may be incorporated into the capillaries and allowed to set when cooled to room temperature. It will be apparent to the skilled addressee that room temperature is commonly regarded as around 20° C. Alternatively, the capillaries may be filled with a material which is deposited as a liquid and which subsequently solidifies. In such embodiments, the solidification may be dependent or independent of heat. It will be apparent that solidification of a liquid filled capillary may be achieved in a number of ways.

For example solidification may take place due to one or more of the following:
  Cooling—the filling may be molten when deposited which then cools to a solid at room temperature;
  Heating—the filling may be liquid when deposited, and the heat of the extruded body portion sets the filling (e.g. pumping egg albumen into a hot hard candy extruded body portion will set the egg on contact);
  Drying—the filling may be a solution that dries into a solid (e.g. the moisture from the solution is absorbed into the extruded body portion);
  Solvent loss—the filling may be in a solvent, whereby the solvent is absorbed into the extruded body portion, leaving a solid;
  Chemical reaction—the filling may be deposited as a liquid but reacts or "goes off" into a solid;
  Cross-linking—the filling may form a constituents for a cross-linked material due to mixing and/or heating; and
  Time—the filling may simply set with time (e.g. a solution of sugars and gelatin will eventually set over time).

The body portion may be formed from a material which is liquid during extrusion. It should be understood that the term "liquid" is intended to mean that the material is capable or has a readiness to flow, including gels, pastes and plasticized chocolate. Furthermore, this term is intended to include (but not limited to) those materials which may be "molten" during extrusion and the skilled addressee will understand that the term "molten" means that the material has been reduced to a liquid form or a form which exhibits the properties of a liquid.

The body portion may be at least partially or substantially solid, so that it can no longer be considered to flow in a liquid form.

Suitable filling materials for the capillaries include, but are not limited to, aqueous media, fats, chocolate, caramel, cocoa butter, fondant, syrups, peanut butter, jam, jelly, gels, truffle, praline, chewy candy, hard candy or any combination or mixture thereof.

If desired, the product may further comprise a coating portion to envelop the body portion. The skilled addressee will appreciate that a number of coatings could be employed—for example chocolate, gum, candy and sugar etc.

The body portion may be connected to one or more further confectionery portions. In some embodiments, the body portion is sandwiched between confectionery materials or may be connected or laminated to one or more confectionery layers. The further confectionery portion or portions may or may not contain inclusions, liquid-filled beads etc.

In some embodiments, the capillaries are distributed substantially uniformly throughout the body portion, and may be spaced evenly apart from adjacent capillaries. In other embodiments, the capillaries may be distributed in pre-defined configurations within the body portion, such as around the periphery of the body portion, or in groups at one or more locations within the body. In some embodiments the body portion has a circular, elliptical, regular polygonal or semi-circular cross-section. The body portion may be shaped in the form of a cylinder, a rope, a filament, a strip, a ribbon or the like, or may be shaped in the form of a standard confectionery product such a chocolate bar, or chewing gum slab, pellet, ball, stick or ribbon, for example. The body portion may be irregular or regular in shape. Furthermore, the body portion may be formed in potentially any shape, for example in the shape of an object, cartoon character or an animal to name a few.

Two or more capillaries may have different widths or diameters. Such an arrangement will allow, if desired, for different quantities of different fill materials to be incorporated into different capillaries. Furthermore, the two or more capillaries may have different cross-sectional profiles. For example, the confectionery product may have capillaries having a cross-sectional shapes including stars and triangles, or different shapes of animals etc.

In an embodiment, the capillaries in the body portion result in a voidage in the range of 1-99% of the extrudate, or 5-99% of the extrudate. The voidage may be in the range of 10-60%, 20-50%, 30-45%, or 35-40%. The voidage may also be in intermediate points in these ranges, for example, 5-40%, 5-45%, 5-50%, 5-60%, 10-40%, 10-45%, 10-50%, 10-99%, 20-60%, 20-45%, 20-40%, 20-60%, 20-99%, 30-40%, 30-50%, 30-60% or 30-99%. The voidage may be over 5%, 10%, 15%, 20%, 25%, 30%, 35%, 40%, 45%, 50%, 55%, 60%, 65%, 70%, 75%, 80%, 85%, 90% or 95%.

The incorporation of capillaries of a small cross-sectional width or diameter enables the capillaries to entrain contrasting or complementary confectionery materials into the body portion whilst avoiding the need to incorporate large centre-fill areas which may be prone to leakage through, or out of, the confectionery product. The use of a plurality of capillaries also enables two or more materials to be incorporated into the confectionery product to give multiple textures, tastes, colours, mouth-feel sensations, temporal profiles and/or sensorial profiles, throughout the whole confectionery product.

In some embodiments, the capillaries have an average diameter or width of no more than, 3 millimeters, 2 millimeters, 1 millimeters, 0.5 millimeters, 0.25 millimeters, or less. It is possible to have capillaries having a diameter or width of no more than 100 micrometers, 50 micrometers, or 10 micrometers. The capillaries may have different widths or diameters if desired.

In another embodiment of the present invention, there is provided a confectionery product comprising a first extruded portion and a second extruded portion, wherein each portion has a plurality of capillaries disposed therein, and the capillaries of the first and second portions are:
  a) discontinuous; and/or
  b) continuous and oriented in more than one direction.

There may be further portions in addition to the first and second portions, which may or may not comprise capillaries. In one embodiment, the confectionery product comprises the first portion separated from the second portion by one or more further portions that may or may not contain capillaries.

The first and second portions may be as described hereinabove for the body portion. The first and second portions may comprise the same material or different materials. For example, the first portion may be chocolate and the second portion candy. The capillaries in each of the first and second portions may be filled with the same or different materials. One or more capillaries in the first and/or second portions may be filled with different material(s) to other capillaries in the first and/or second portion.

According to a further embodiment of the invention, there is provided a confectionery product comprising an extruded body portion having a plurality of capillaries disposed therein, wherein each capillary is separated from each adjacent capillary by a wall formed from the extruded body portion and wherein the wall between each capillary has a thickness of no more than the width or diameter of the capillaries.

In some embodiments of the present invention, the plurality of capillaries disposed in the body portion of the confectionery product may be anywhere from 2-50 capillaries, from 5-50 capillaries, from 10-40 capillaries, from 20-40 capillaries or from 30-40 capillaries. The capillaries may result in a voidage in the range of about 5-40%, or about 10-40%, or about 20-40%, or about 30-40%, of the extrudate. The capillaries may have an average diameter or width of about 0.1-5 mm. In some embodiments, such as some embodiments that do not employ further stretching of the extrudate, the average diameter or width of the capillaries may be, for instance, about 0.5-5 mm. In some other embodiments, such as some embodiments employing further stretching of the extrudate, the average diameter or width of the capillaries may be reduced, for instance, to about 0.1-1 mm.

In some embodiments, the wall or separation between each capillary may have a thickness of about 0.1-3 mm. In seine embodiments, such as some embodiments that do not employ further stretching of the extrudate, the wall between each capillary may have a thickness of about 0.5-3 mm. In some other embodiments, such as some embodiments employing further stretching of the extrudate, the wall between each capillary may be reduced to a thickness of about 0.1-2.5 mm, or about 0.1-1 mm in some embodiments.

In some embodiments, the plurality of capillaries may be centrally grouped within the extruded body portion and surrounded by an outer wall that extends to the outer surface of the body portion. In such embodiments, the outer wall may have a thickness of about 0.1-5 mm. In some embodiments, such as some embodiments that do not employ further stretching of the extrudate, the outer wall may have a thickness of about 0.5-5 mm. In some other embodiments, such as some embodiments employing further stretching of the extrudate, the outer wall may be reduced to a thickness of about 0.1-1 mm.

In addition, in some embodiments, the final piece weight of the individual confectionery products formed from the extrudate may be about 1-10 g and the cross-sectional size may be anywhere from about 5-30 mm, for instance, a circular cross-section having a diameter of about 10-30 mm.

According to a further embodiment, there is provided a process for manufacturing a confectionery product comprising a body portion, having a plurality of capillaries disposed therein, the process comprising the steps of:
  a) extruding an extrudable confectionery material with a plurality of capillaries disposed therein; and
  b) at least partially filling one or more capillaries with a fill material which is a different material from that of the extruded body portion, the fill material comprising an active and/or reactive component and wherein two or more different active/reactive components are provided in the same or different capillaries.

In some embodiments, the method may include an extra step selected from:
  c) cutting the extrudate into two or more pieces having a plurality of capillaries disposed therein and forming a confectionery product incorporating the pieces; and/or
  d) folding the extrudate and forming a confectionery product incorporating the folded extrudate.

According to a further embodiment, there is provided a process for manufacturing a confectionery product comprising a body portion, having a plurality of capillaries disposed therein, the process comprising the steps of:
  a) extruding an extrudable confectionery material with a plurality of capillaries disposed therein; and
  b) cutting the extrudate into two or more pieces having a plurality of capillaries disposed therein and forming a confectionery product incorporating the pieces; or
  c) folding the extrudate and forming a confectionery product incorporating the folded extrudate The deposition of the filling may be during the step of extrusion—but could also take place after extrusion. In an embodiment, the filling comprises a fluid. The fluid may comprises a liquid, or a material which is liquid at a temperature greater than room temperature. The fluid may solidify after deposition is desired.

The two or more capillaries may be at least partially filled with different active and/or reactive materials. The active and/or reactive component may be encapsulated. The active and/or reactive component may comprise an effervescent material. The fill material may comprise particulate material. The fill material can comprise any number of materials as described herein above with reference to the product itself.

The extrudable material will preferably be liquid during extrusion.

According to a further embodiment, there is provided a process for manufacturing a confectionery product including an extruded body portion having a plurality of capillaries disposed therein, the process including the steps of:
  a) extruding an extrudable confectionery material with a plurality of capillaries disposed therein; and
  b) at least partially filling one or more of the capillaries with a fill material;
  wherein the product includes a first sensate and a second sensate which is different from the first sensate located in separate and discrete regions of the product and being adapted to provide sequential release profiles.

In some embodiments, the process may include an extra step selected from:
  c) cutting the extrudate into two or more pieces having a plurality of capillaries disposed therein and forming a confectionery product incorporating the pieces; and/or
  d) folding the extrudate and forming a confectionery product incorporating the folded extrudate.

In another embodiment, there is provided a process for manufacturing a confectionery product including an extruded body portion having a plurality of capillaries disposed therein, the process including the steps of
  a) extruding an extrudable confectionery material with a plurality of capillaries disposed therein at temperatures of 50° C. or higher; and
  b) at least partially filling one or more capillaries with a fill material which is a different material from that of the extruded body portion during or subsequent to said extrusion step (a), the fill material including an active and/or reactive component that is volatile at temperatures of 35° C. and higher, wherein the extruded body portion is essentially free of the volatile active and/or reactive component.

In some embodiments, the filling step (b) includes at least partially filling the capillaries with a fill material at a temperature of less than 50° C.

In another embodiment, there is provided a process for manufacturing a confectionery product including an extruded body portion having a plurality of capillaries disposed therein, the process including the steps of:
a) extruding an extrudable confectionery material with a plurality of capillaries disposed therein at temperatures of 50° C. or higher; and
b) at least partially filling one or more capillaries disposed in the extruded body portion with a fill material which is a different material from that of the extruded body portion during or subsequent to said extrusion step (b), the fill material including an active and/or reactive component that degrades when subjected to manufacturing conditions including exposure to temperatures of 50° C. and higher,
wherein the extruded body portion is essentially free of the degradable active and/or reactive component.

In some embodiments, the filling step (b) includes at least partially filling the capillaries with a fill material at a temperature less than 50° C.

In a further embodiment, there is provided a process for manufacturing a confectionery product for imparting a perception of satiety including an extruded body portion having a plurality of capillaries disposed therein, the process including the steps of:
a) extruding an extrudable confectionery material with a plurality of capillaries disposed therein; and
b) at least partially filling one or more of the capillaries with a fill material including a satiety agent and wherein two or more different satiety agents are provided in the same or different capillaries, the satiety agents being selected from sweet flavors, savory flavors, green tea extract, caffeine, fibers, proteins and lipids.

In yet another embodiment, there is provided a process for manufacturing a dental cleaning chewing gum product including an extruded body portion having a plurality of capillaries disposed therein, the process including the steps of:
a) extruding an extrudable confectionery material with a plurality of capillaries disposed therein; and
b) at least partially filling one or more of the capillaries with a fill material,
wherein the product includes two or more different dental cleaning agents located in the same or different regions of the product.

Any of the processes may further comprise the step of quench cooling the extrudate after extrusion. The quench cooling may utilise a fluid, such as air, an oil or liquid nitrogen—but other methods of quench cooling will also be apparent to the skilled addressee.

Any of the processes may further comprise the step of, after extrusion, stretching the extrudate. Stretching the extrudate may be undertaken by a number of means, for example passing the extrudate over, or through conveyor belts or rollers operating at different speeds, so as to stretch the extrudate. By employing this additional step, extrusions having capillaries of a larger diameter, width, cross-sectional area, etc. can be produced, which can be reduced in size gradually over time so as to produce an extrudate with smaller capillaries which would have been more difficult to initially. Commonly, capillaries having a bore size of 2 mm or more will be produced during extrusion and these capillaries will be reduced significantly by stretching the extrudate. In some embodiments the capillaries are reduced to no more than 1 mm, 0.5 mm, 0.25 mm, 100 µm, 50 µm, 25 µm or 10 µm.

The extrudable confectionery material will at least partially or substantially solidify after extrusion.

If desired, two or more capillaries may be formed having different widths or diameters. Furthermore, two or more of the capillaries may be formed having different cross-sectional profiles.

Any of the processes may further comprise the step of enveloping the confectionery product in a coating. Such a coating will be apparent to the skilled addressee and discussed previously.

The processes may be used for producing a confectionery material as herein above described.

A further embodiment of the present invention provides for apparatus which is adapted for producing a confectionery product according to the processes as herein above described. WO2005056272 discloses an apparatus for producing an extrudated product including a plurality of channels. WO2008044122 discloses a related apparatus, which additionally includes means for quench cooling an extrudate as it exits the die. Both of these apparatus may be employed/adapted for use in producing the confectionery in accordance with the present invention.

The extrusion die employed in the apparatus can be a ribbon die, matrix die, annular die or circular die. Different dies can be used to produce different extruded product shapes and different amounts and patterns of the capillaries. In particular, different dies can have different numbers of needles, thereby providing extruded products with different amounts of capillaries disposed therein. The needles also may have different cross-sectional profiles, thereby providing extruded products with various shapes and patterns of the capillaries. For instance, in some embodiments, a die may have anywhere from 2-50 needles. In some embodiments, the die may have a smaller number of needles, such as for instance 3-5 needles. In some other embodiments, the die may have a larger number of needles, such as for instance 20-40 needles, or 30-40 needles in some embodiments. For example, the matrix die shown in FIG. 29 contains 30 needles having an inner diameter of 0.5 mm. The circular die shown in FIGS. 30-31 contains 37 needles having an inner diameter of 1.1 mm.

In addition, the apparatus can include a flange surrounding the die and defining the orifice of the extrusion apparatus. Different flanges can be employed to form different outer shapes of the extrudate. The flange also can define the distance between the plurality of capillaries and the outer surface of the extrudate. For instance, the plurality of capillaries may be centrally grouped within the extruded body portion and surrounded by an outer wall that extends to the outer surface of the body portion. The thickness of the outer wall can be determined by the size of the flange.

In some embodiments, the extrusion die may include a rotary valve that is adapted to rotate to create swirl-type patterns of capillaries within the body portion. For instance, in one embodiment, the capillaries may swirl around a center-fill region of the product. An example of a rotary valve, which could be employed/adapted for use herein, is disclosed in International Publication No. WO2008048881A2, which is incorporated by reference herein.

DETAILED DESCRIPTION OF THE INVENTION

Specific embodiments of the present invention will now be described, by way of example only, with reference to the accompanying drawings, in which.

Figure 1:
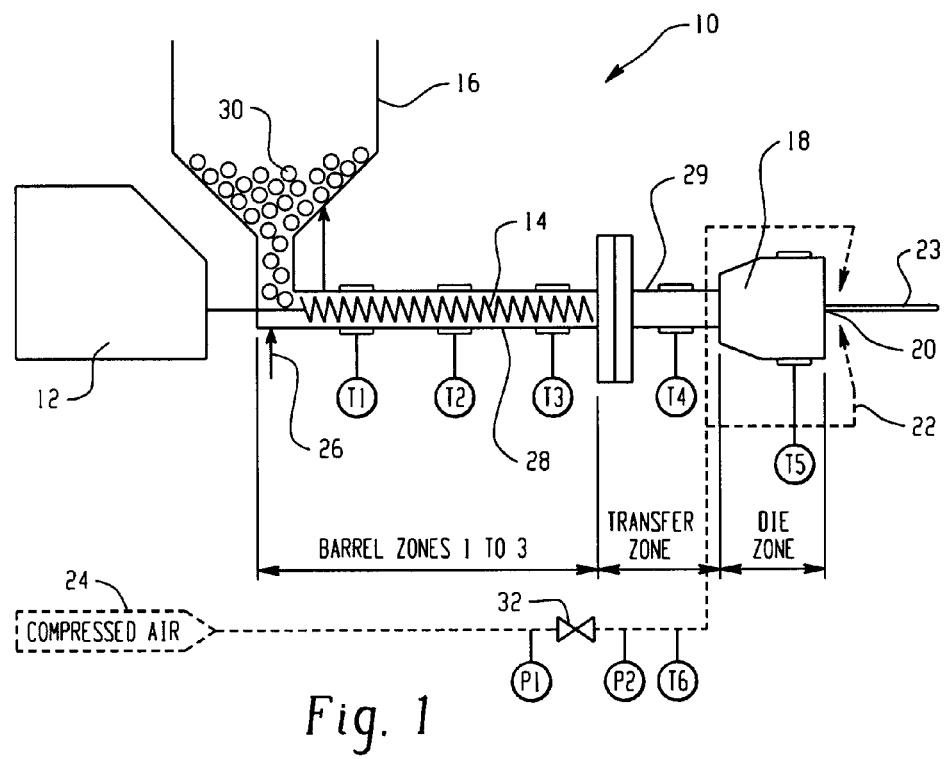
FIG. 1 is a schematic diagram illustrating the overall apparatus used for the experiments described in Examples 1 and 2, in accordance with the present invention.
Figure 2:
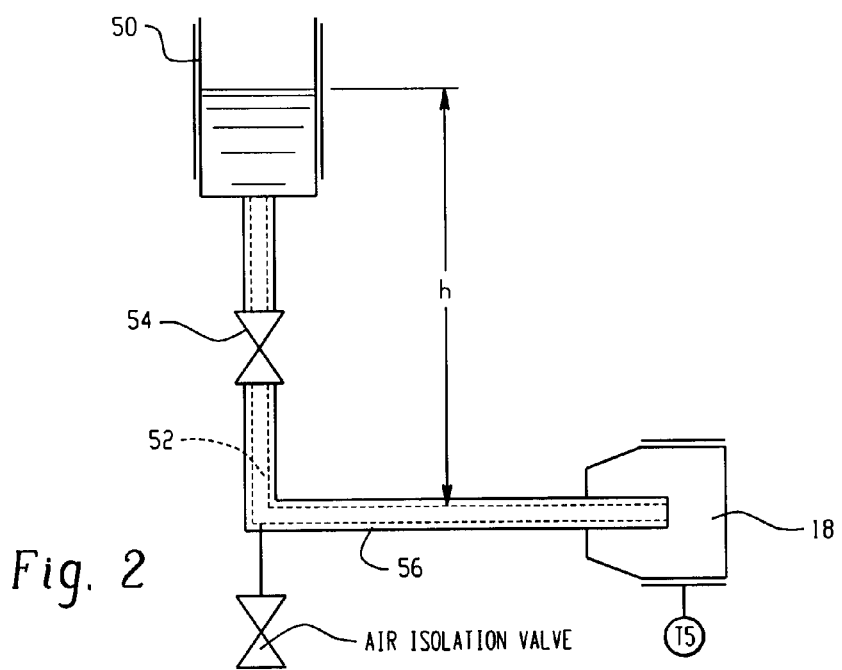
FIG. 2 is a schematic diagram illustrating the apparatus which can be used in conjunction with the apparatus shown in FIG. 1, so as to provide a liquid filled capillaries.
Figure 6A:
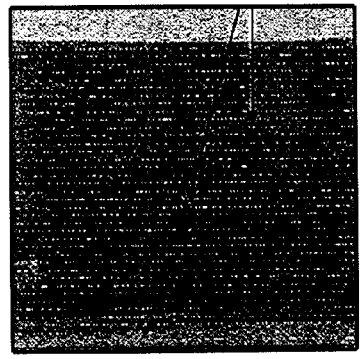
Figure 6B:
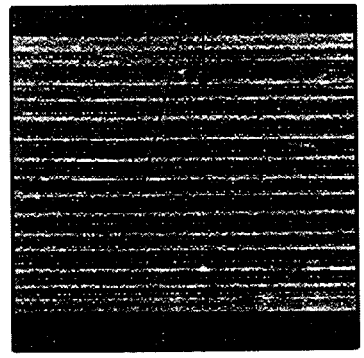
Figure 7:
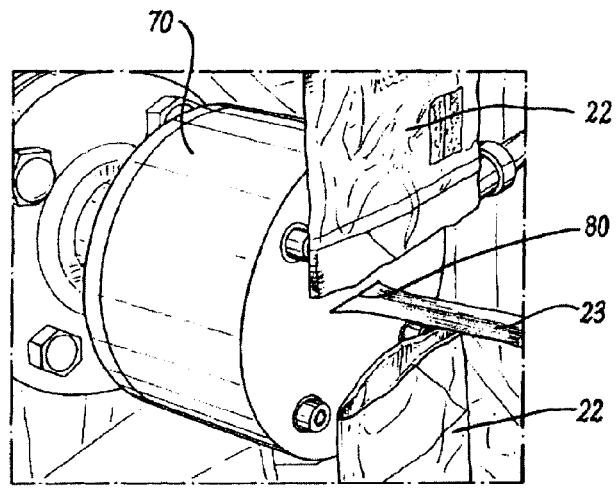
Figure 8:
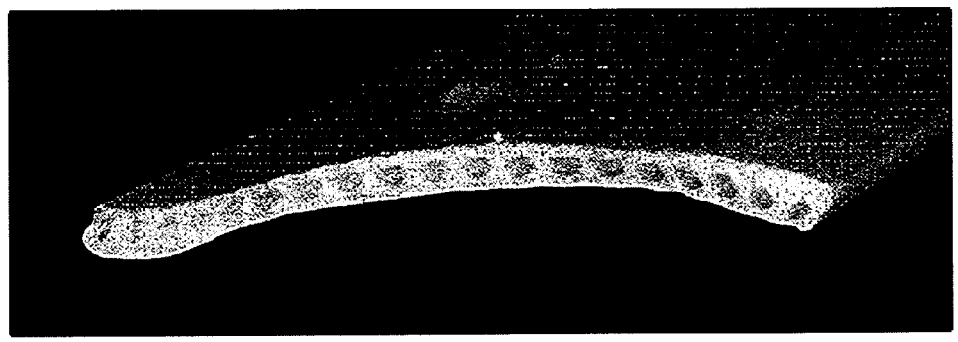
Figure 9:
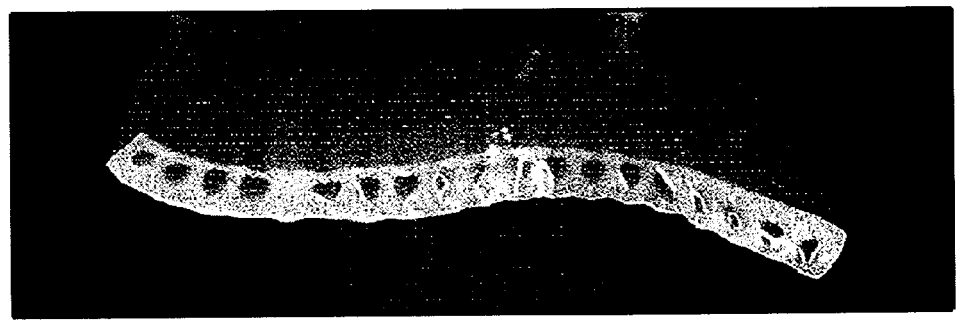
Figure 10:
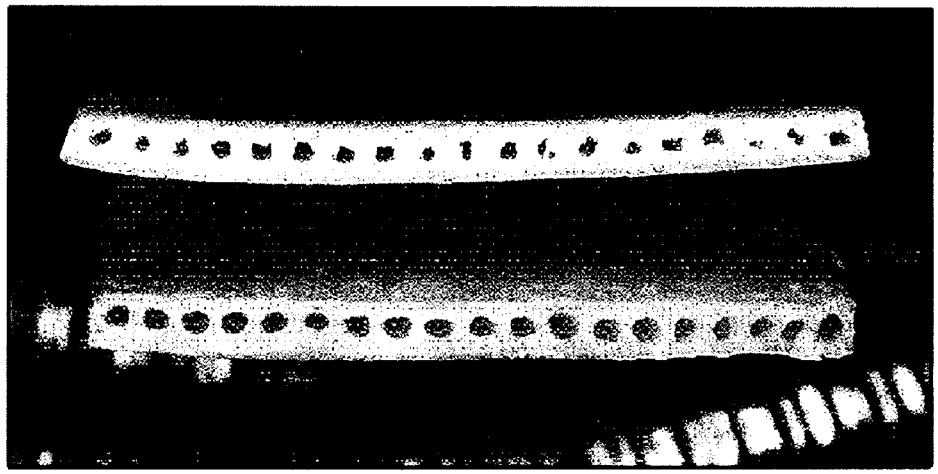
Figure 11:
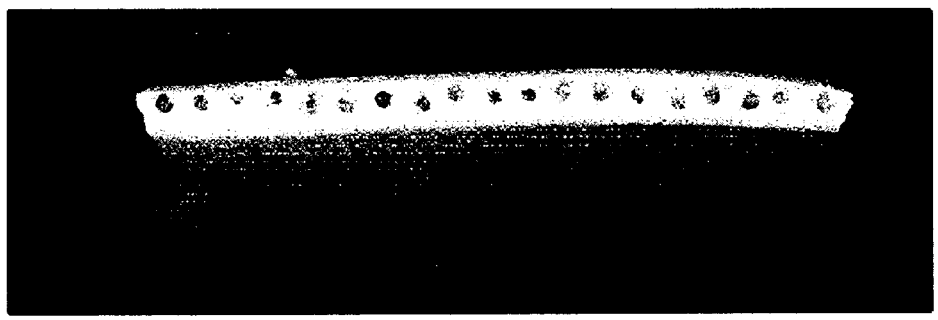
Figure 12:
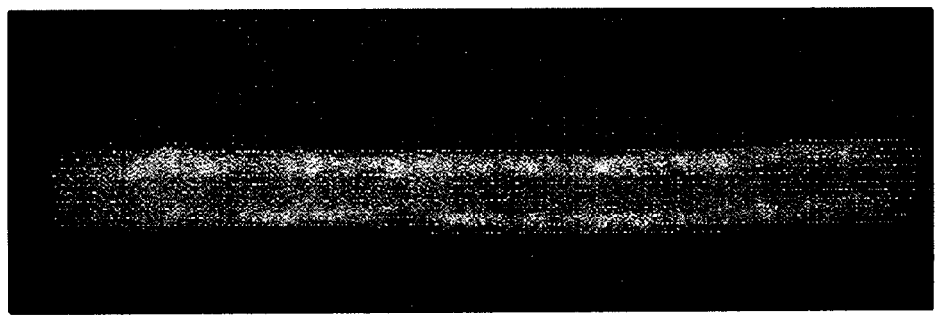
Figure 13:
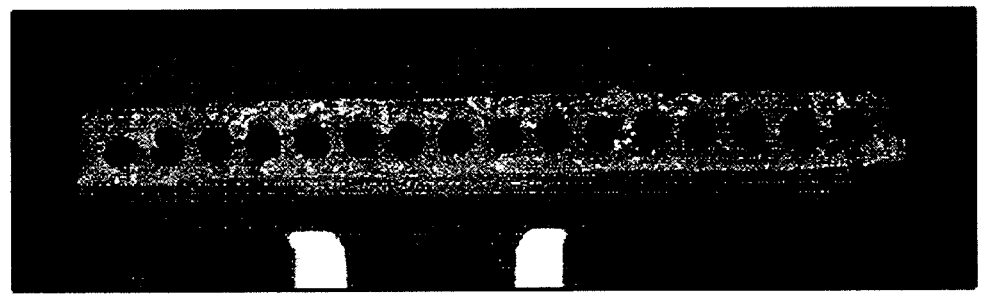
Figure 14:
Figure 15A:
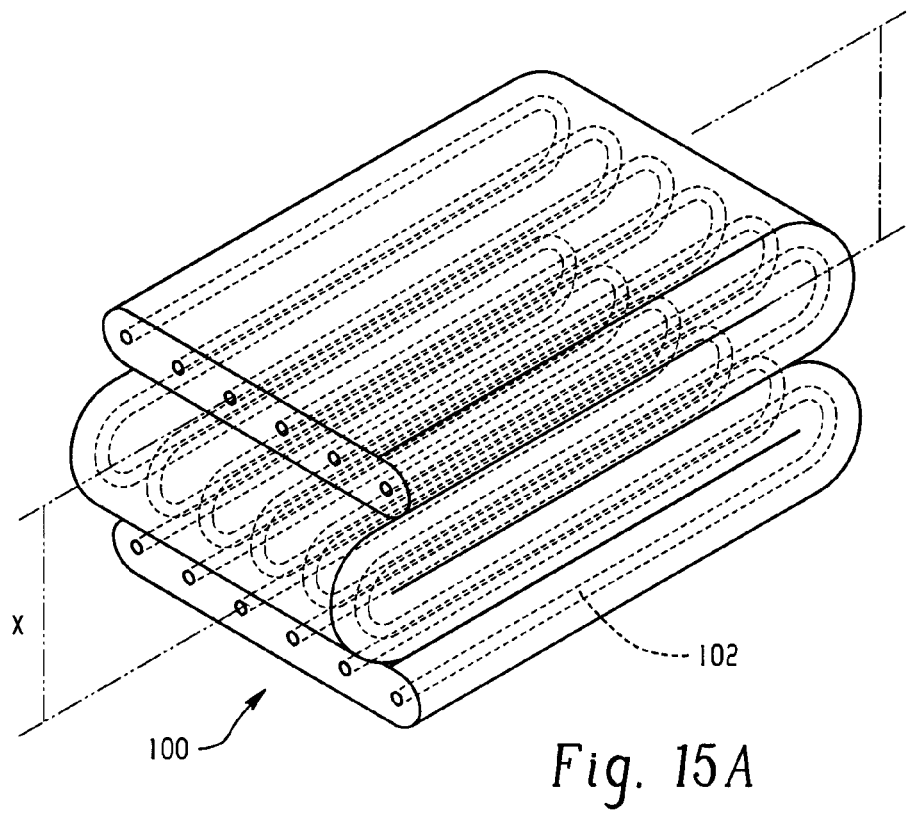
Figure 15B:
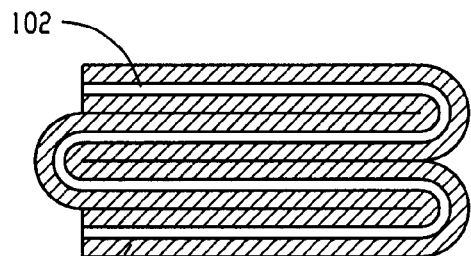
Figure 16:
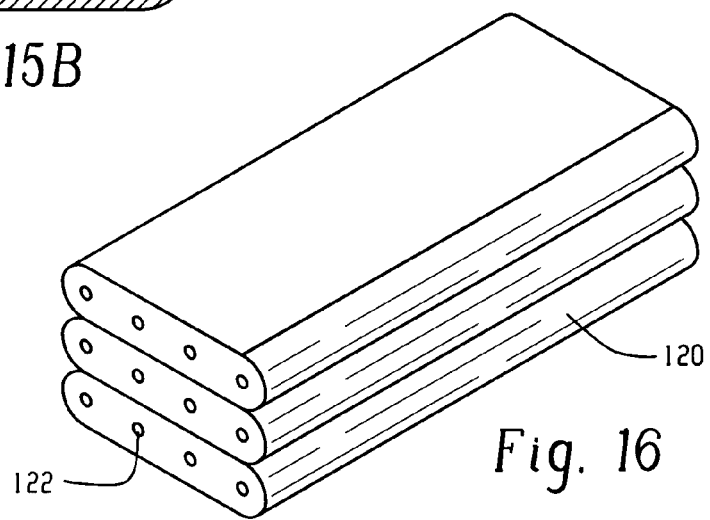
Figure 17:
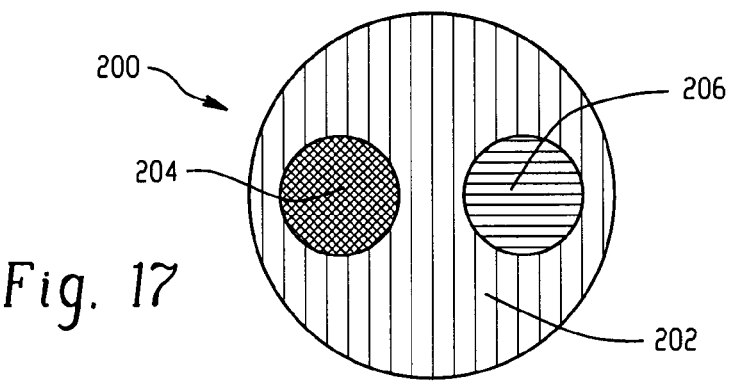
Figure 18:
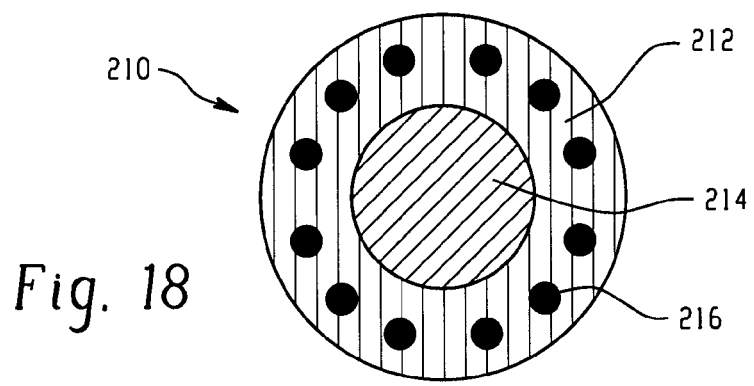
Figure 19:
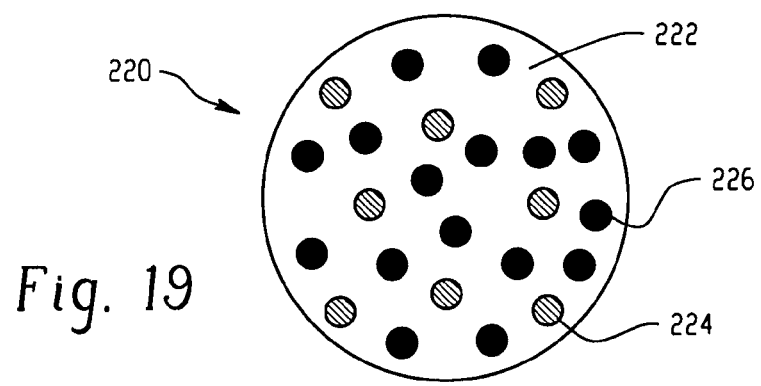
Figure 20:
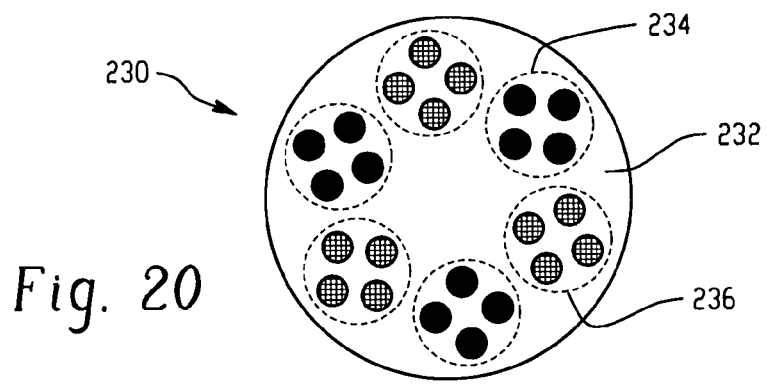
Figure 21:
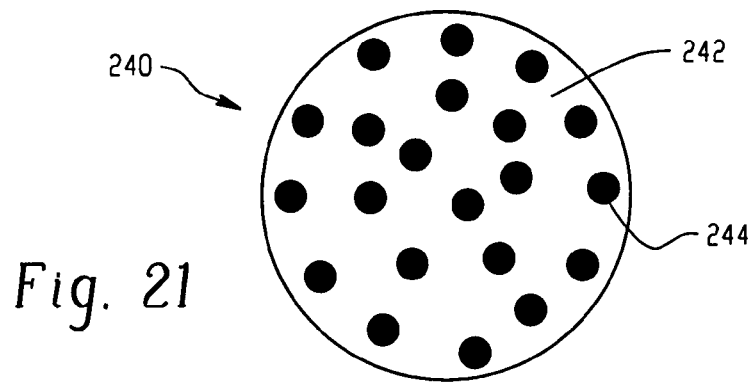
Figure 22:
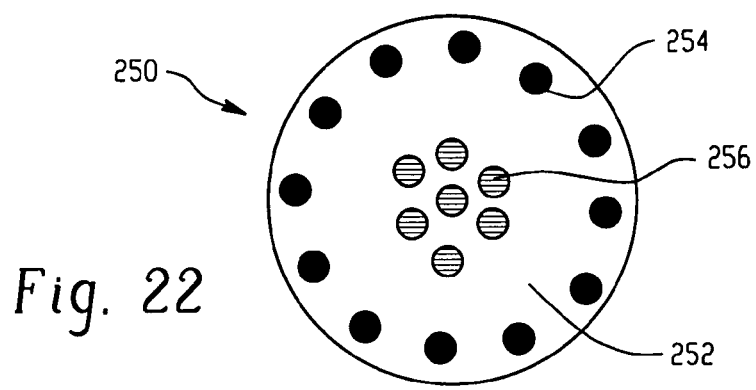
Figure 23:
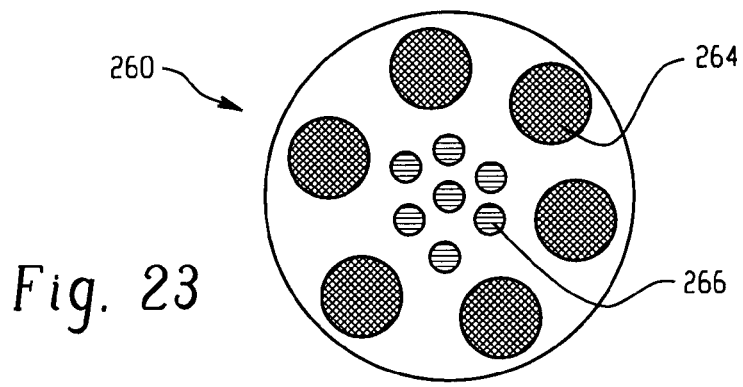
Figure 24:
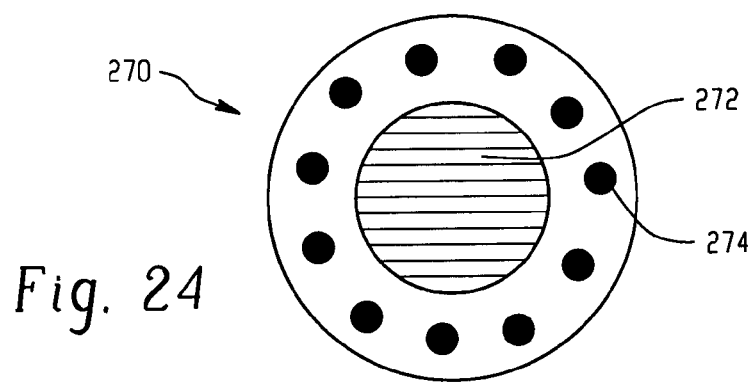
Figure 25:
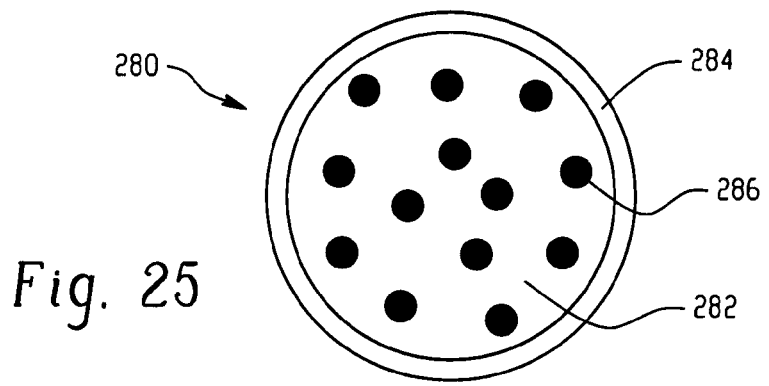
Figure 26:
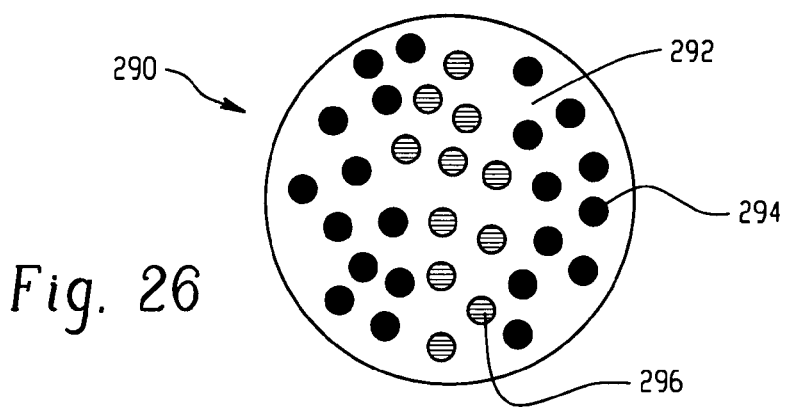
Figure 27:
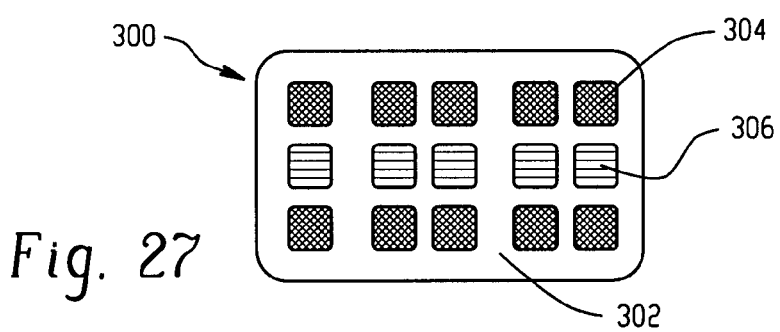

FIGS. 5A, 5B, 5C, and 5D shows photographs of four capillary extrudates formed from material 1 in Example 1, the photographs show: (A) low voidage, (B) and (C) high voidage and (D) very high voidage;

FIGS. 6A and 6B shows photographs comparing capillary extrudates formed from (A) material 2 containing completely filled cocoa butter capillaries and (B) material 1 formed with air filled capillaries;

FIG. 7 is a line drawing of the external part of the extrusion apparatus as illustrated in FIGS. 1 and 2, showing the air knives used to cool the extrudate when it exist the die;

FIG. 8 shows a hard candy with an air fill produced in Example 2, in accordance with the present invention;

FIG. 9 shows a hard candy with a liquid fill produced in Example 2, in accordance with the present invention;

FIG. 10 shows a gum with an air fill, produced in Example 2, in accordance with the present invention;

FIG. 11 shows a gum with a liquid fill, produced in Example 2, in accordance with the present invention;

FIG. 12 shows a gum with a solid fill, produced in Example 2, in accordance with the present invention;

FIG. 13 shows a chocolate with an air fill, produced in Example 2, in accordance with the present invention;

FIG. 14 shows a chocolate with an air fill as shown in FIG. 13, but in longitudinal cross section;

FIG. 15A shows a perspective view of an extrudate formed in accordance with the present invention, where the extrudate has been folded;

FIG. 15B shows a cross-sectional view of the extrudate as shown in FIG. 15A, viewed from the line denoted "X";

FIG. 16 shows a perspective view of an extrudate formed in accordance with the present invention, where a number of extrudated layers have been stacked upon one another;

FIG. 17 shows a cross-sectional view of an embodiment of a confectionery product in accordance with the present invention, where the product has two capillaries, each of which containing a different fill material;

FIG. 18 shows a cross-sectional view of an embodiment of a confectionery product in accordance with the present invention, where the product has a plurality of capillaries positioned around the periphery of the product containing a first fill material, and a second centrally located capillary containing a second fill material;

FIG. 19 shows a cross-sectional view of an embodiment of a confectionery product in accordance with the present invention, where the product has a plurality of capillaries positioned throughout the product and the capillaries contain one of two fill materials;

FIG. 20 shows a cross-sectional view of an embodiment of a confectionery product in accordance with the present invention, where discrete groups of four capillaries are formed around the periphery of the product;

FIG. 21 shows a cross-sectional view of an embodiment of a confectionery product in accordance with the present invention, where the product has a plurality of capillaries positioned throughout the product, and the body portion contains a first sensate whereas the capillaries contain a second and different sensate;

FIG. 22 shows a cross-sectional view of an embodiment of a confectionery product in accordance with the present invention, where the product has two groups of capillaries, and the first group contains a first sensate and the second group contains a second and different sensate;

FIG. 23 shows a cross-sectional view of another embodiment of a confectionery product in accordance with the present invention, where the product has two groups of capillaries, the first group containing a first sensate and the second group containing a second and different sensate;

FIG. 24 shows a cross-sectional view of an embodiment of a confectionery product in accordance with the present invention, where the product has a center-fill region containing a first sensate, and a plurality of capillaries positioned around the periphery of the body portion containing a second and different sensate;

FIG. 25 shows a cross-sectional view of an embodiment of a confectionery product in accordance with the present invention, where the product is enveloped by a coating containing a first sensate and the product has a plurality of capillaries disposed in the body portion, which contain a second and different sensate;

FIG. 26 shows a cross-sectional view of an embodiment of a confectionery product for imparting a perception of satiety in accordance with the present invention, where the product includes a sweet flavour in the body portion and contains two groups of capillaries disposed therein, one group of capillaries containing a savory flavour and a second group of capillaries containing fiber and/or protein;

FIG. 27 shows a cross-sectional view of an embodiment of a chocolate confectionery product for imparting a perception of satiety in accordance with the present invention, where the product includes caffeine in the body portion and contains two groups of capillaries disposed therein, one group of capillaries containing a sweet flavour and a second group of capillaries containing a savory flavour.

Figure 28:
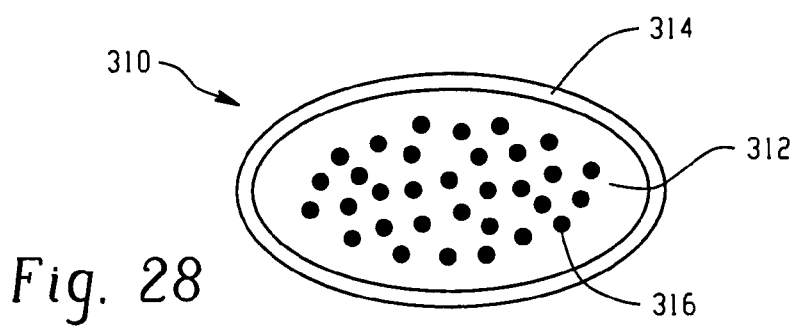

FIG. 28 shows a cross-sectional view of an embodiment of a confectionery product in accordance with the present invention, where the product includes a dental cleaning agent in the body portion and contains a plurality of capillaries disposed therein, the capillaries including a second and different dental cleaning agent.

Figure 29:
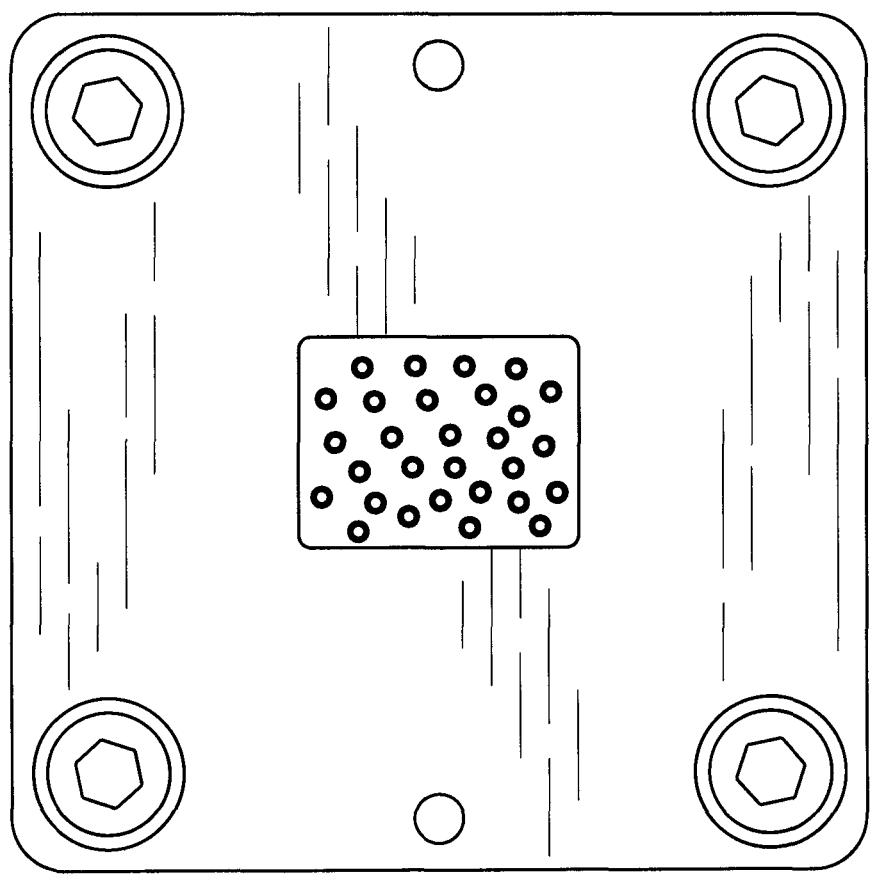
Figure 30:
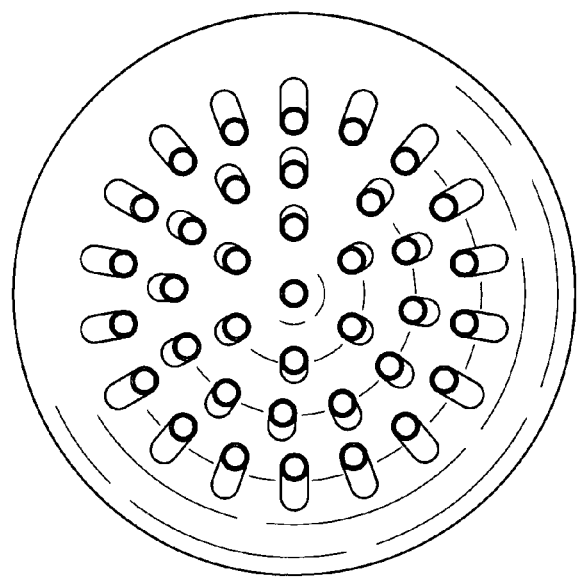
Figure 31:
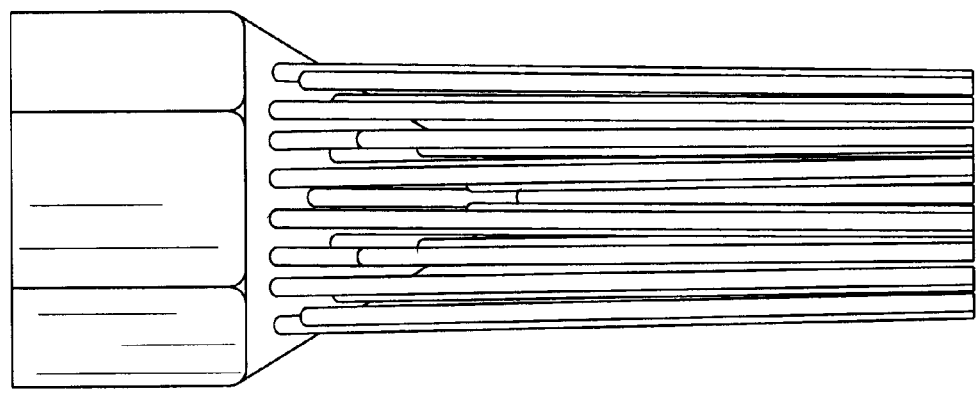

FIG. 29 is a line drawing of a matrix extrusion die that can be used to form capillaries in extruded materials in accordance with some embodiments of the present invention;

FIG. 30 is a line drawing of a circular extrusion die that can be used to form capillaries in extruded materials in accordance with some embodiments of the present invention; and FIG. 31 is a line drawing of a different view of the circular extrusion die shown in the photograph of FIG. 30.

Experiments were conducted to produce a variety of confectionery products incorporating capillaries. Three phases of extrusion work were undertaken using various materials. The first phase concerned the extrusion of hard candy using a capillary die attached to a small-scale extruder in a non-food grade environment for creating capillary candy extrudates in both low- and high-voidage forms.

The second phase of the experimental work built upon the first phase to produce low and high voidage candy capillary extrudates containing an array of cocoa-butter filled capillaries. The first and second phases are described below in Example 1. The third phase built upon the first two and recreated the working environment with food grade equipment in a food grade environment and is described below in Example 2.

Example 1

Phase one concerned the extrusion of candy using a capillary die attached to a small-scale extruder, in order to confirm that candy having capillaries with both low and high voidage values could be formed in accordance with the present invention.

The materials that were trialled during this investigation are shown in Table 1.

TABLE 1

Materials tested.

| Material number | Material name | Majority ingredients | Application |
| --- | --- | --- | --- |
| 1 | Custom recipe 1 | Sugar (40%) Glucose Syrup (60%) | Extruded matrix |
| 2 | Custom recipe 2 | Maltitol syrup (96%) Gum Arabic (2%) Water (2%) | Extruded matrix |
| 3 | Cocoa butter | Cocoa butter (100%) | Capillary filler |

Materials 1 and 2 were supplied as large solid blocks. All materials were crushed prior to extrusion to yield a fine granular powder, with grain sizes ranging between 1 mm and 5 mm. Material 3 was supplied as a tub of solidified cocoa butter; the required quantity was broken up into a fine powder containing only small lumps before being fed into the heated cocoa butter reservoir.

The extrusion equipment consisted of a Betol single screw extruder, with a screw diameter of approximately 12 mm, and a screw L/D ratio of roughly 22.5:1. The extruder had four different temperature zones (denoted T1-T4 in FIG. 1 as described later), each of which could be independently controlled using PID controllers connected to band heaters. The Mk 3 MCF extrusion die, containing an entrainment array consisting of 17 hypodermic needles, was connected on the extruder endplate. Two opposed air jets, used to rapidly quench the extrudate emerging from the extrusion die, were placed above and below the die exit; these jets were connected via a valve to a compressed air line at 6 Barg. A schematic diagram showing the general layout of the extrusion line is shown in FIG. 1 and a schematic drawing of the capillary die is shown in FIG. 2.

With reference to FIG. 1, there is shown a schematic diagram of the extrusion apparatus 10 used in the experiments. The apparatus briefly comprises an electric motor 12 which is rotatably coupled to an extrusion screw 14. The screw 14 is fed at one end by a hopper 16 and the opposing end is coupled to an extrusion die 18 having an extrudate outlet 20. Quench jets 22 are directed towards the die outlet 20 so as to cool the extruded material 23 which is produced and these jets are fed with compressed air 24. If desired, the area of the apparatus where the hopper 16 is coupled to the screw 14 can be cooled by means of a cooling feed 26. Surrounding the screw 14 is a barrel 28 which is formed having three barrel temperature zones denoted T1 to T3—the temperatures of each zone being capable of being controlled. The barrel 28 is connected to the die 18 by means of a feed conduit 29 which also has a temperature zone T4 which can be controlled.

In use, the hopper 16 is filled with material 30 (such as candy in solution) which can be heated so as to render it (or maintain it as) a liquid (not solid or solid particulate). Before the material passes into the screw 14, it can be cooled by means of the cool feed 26, so as to ensure that the material is at the correct temperature for entering the screw extruder. As the screw is rotated, the liquid material is drawn along the screw 14, inside the barrel 28 and the temperature of the zones T1-T3 adjusted accordingly. The material then passes through the feed conduit 29 and the temperature adjusted again (if required) by temperature control T4 before entering the die 18. The die 18 (shown in FIG. 3) has a number of needles (not shown) located within an entrainment body so that the material passes over and around the needles. At the same time that the material is being extruded, compressed air 24 is forced through the needles so that the extrudate contains a number of capillaries. The extrudate 23 is cooled by means of the quench jets 22 as it is released from the die 18. A valve 32 controls the flow of compressed air to the apparatus and pressure devices P1 and P2 control the pressure of the compressed air 24 before and after the valve. The compressed air line also has a temperature control T6 so as to control the temperature of the air before entering the die.

With reference to FIG. 2, there is shown an adaptation of the apparatus shown in FIG. 1. Rather than compressed air 24 being forced through needles, the needles are connected to a reservoir 50 containing cocoa butter. The reservoir 50 is heated so that the cocoa butter is maintained at the correct temperature so as to maintain it in a liquid state. The reservoir 50 is connected to a conduit 52 having an isolation valve 54 for controlling the flow of liquid. The conduit 52 is encased in a trace heating tube 56 which maintains the temperature of the conduit so that the liquid remains in a liquid state during its movement within the conduit. The conduit 52 is coupled to the inlet to the die 18 having number of needles, so that when the material is being extruded, the capillaries formed around and the needles can be simultaneously filled with cocoa butter. Of course, the capillaries could be filled with other types of liquid material if desired.

Figure 3:
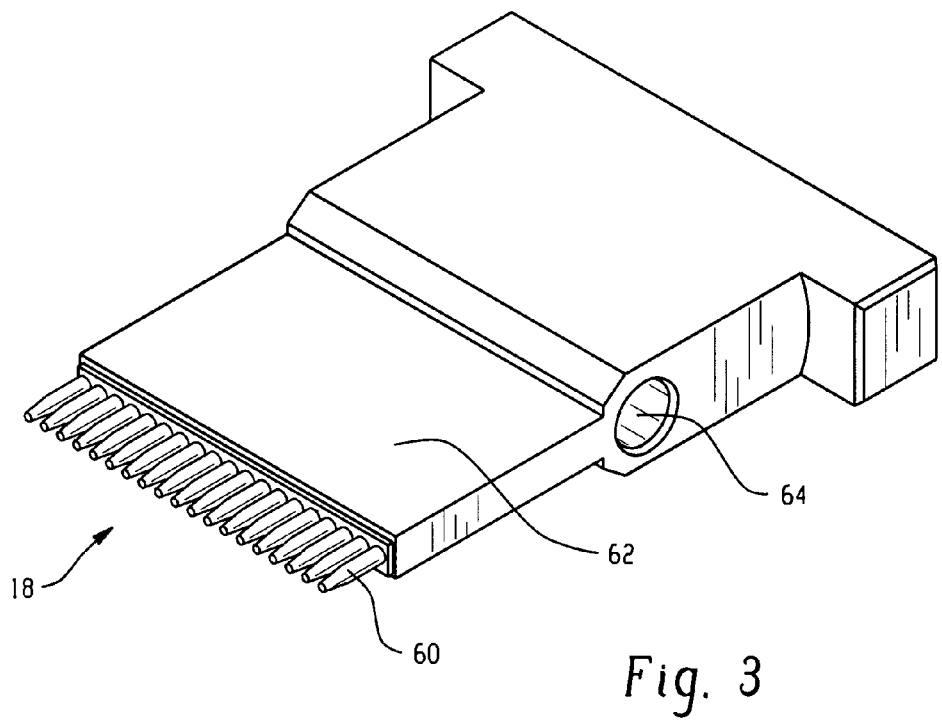
FIG. 3 is a photograph of the extrusion die used to form capillaries in the extruded material of Examples 1 and 2.

FIG. 3 shows the die 18 in more detail. In particular, this figure shows that the metallic die 18 has, at one end, a plurality of needles 60 which are joined to a cavity 62 which is in fluid communication with an inlet channel 64 for pumping a fluid material into the capillaries of the extrusion.

In some alternative embodiments of the present invention, the die employed in the apparatus can be a matrix die, annular die or circular die instead of the ribbon die used in this experiment. Different dies can be used to produce different extruded product shapes and different amounts and designs of the capillaries. FIG. 29 shows a matrix die suitable for use in some embodiments of the present invention. The matrix die shown in FIG. 29 contains 30 needles having a diameter of 0.5 mm. FIGS. 30-31 show a circular die suitable for use in some embodiments of the present invention. The circular die shown in FIGS. 30-31 contains 37 needles having a diameter of 1.1 mm.

Figure 4:
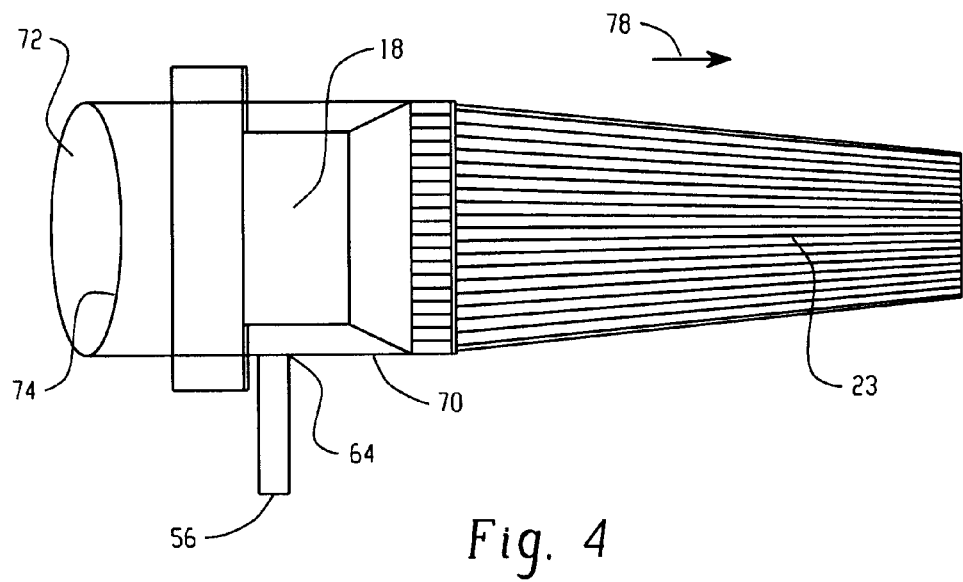
FIG. 4 is a plan view of the extrusion die which incorporates the extrusion die shown in FIG. 3 in the apparatus as illustrated in FIGS. 1 and 2.

With reference to FIG. 4, there is shown the die 18 in place in an entrainment body 70. Molten material 72 enters an opening 74 of the entrainment body 70 and the material is forced over and around the needles 60 of the die 18. At the same time, either air or liquid cocoa butter enters the die inlet by means of a fluid feed conduit 56. When operational, the molten material is extruded through the entrainment body 70 over the needles 60 of the die 18. Either air or cocoa butter is then pumped through the needles at the same time so as to produce an extrudate 23 (in direction 78) which either has capillaries with no filling or capillaries filled with cocoa butter.

FIG. 7 shows the entrainment body 70 having an opening 80, through which the extrudate is formed. This figure also shows two quench jets 22 located above and below the aperture so as to cool down the extrudate after is has been produced.

In use, the flow of molten material over the tips of the entrainment nozzles (hypodermic needles) caused a small area of low pressure to form at each needle tip. Each nozzle was connected together via internal channeling within the entrainment body. These, in turn, were connected outside the extrusion die to either air at room temperature and pressure or to a molten cocoa butter reservoir, with a hydraulic head of h in FIG. 2. The pipework connecting the die to the cocoa butter reservoir and the cocoa butter reservoir was externally heated to maintain the cocoa butter in the liquid phase. A set of isolation valves were used to switch between either using an air feed to the entrainment body or a molten cocoa butter feed. This is shown schematically in FIG. 2.

The quench jets were used for the generation of the high-voidage material. Differential scanning calorimetry (DSC) was used to examine the thermal behaviour of the materials, such that information relating to the phase transition temperatures could be obtained.

Material 1 was formed in a large solid block. The block was broken up mechanically, such that it became a granulated material with granule sizes between 1 mm and 5 mm.

The extrusion temperature profile was set to that shown in below Table 2.

TABLE 2

Extruder temperature profile for material 1.

| Temperature zone | Label on FIG. 1 |
| --- | --- |
| Barrel zone 1 | T1 |
| Barrel zone 2 | T2 |
| Barrel zone 3 | T3 |
| Die zone 1 | T4 |
| Die | T5 |

Granulated pieces of material 1 were starve-fed into the extruder, with the extruder screw-speed set to 40 rpm. The granules of material 2 conveyed well into the extruder in the solid phase initially, but due to the sticky nature of the material, some mild feed zone bridging and blocking was observed. This was overcome by gently pushing the broken-up material onto the extruder screw with a polyethylene rod.

Successful capillary extrudates were easily achievable using this protocol. The material had good melt strength and was pulled away easily from the die in the molten state before it set into a brittle, glassy, material. The glassy state of the material meant that it was unsuitable for use in a pair of nip rolls since the compression experienced by the material in this apparatus caused fracture. Consequently, the capillary extrudates from material 1 were hand drawn, the capillaries having an average diameter (width) of less than 4 mm.

Figure 5A:
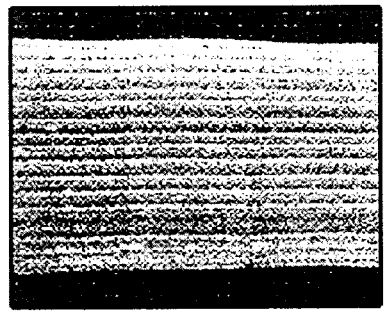
Figure 5C:
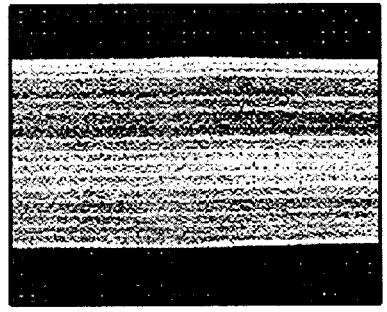
Figure 5B:
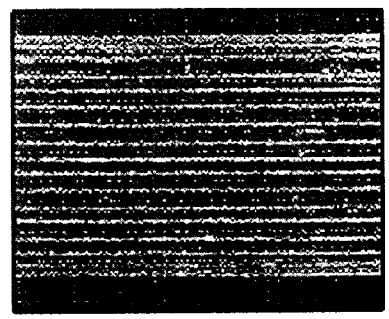
Figure 5D:
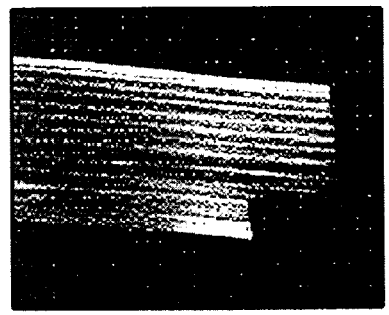

Low voidage MCF from material 1 was easily obtained without quenching the extrudate using the quench jets; this is illustrated in the photograph in FIG. 5(A). Enhanced manual hauling of the extrudate away from the die exit coupled with use of the quench jets resulted in high voidage capillary being extruded. The ultimate voidage depended on the speed at which material is hauled away from the die; various different forms of high voidage capillary extrudate formed from material 1 are shown in FIGS. 5(B), (C) and (D). Crude optical analysis of the cross section of material similar to those shown in FIGS. 10 (B) and (C) revealed that voidage between 35% and 40% had been generated. It is highly likely that the high voidage material shown in FIG. 10 (D) was in excess of the value of 35% to 40%.

The second phase of the of extrusion experiments were conducted with material 1 using cocoa butter heated to between 35° C. and 40° C. The head, h, of the cocoa butter reservoir was initially set to 8 cm, and material two fed into the extruder as described earlier. The initial proof of concept was successful, and resulted in the partial filling of the capillaries with molten cocoa butter. It was observed, however, that due to the increased viscosity of the cocoa butter compared to air, the rate at which cocoa butter could be entrained into the extrudate was slow. This problem appeared to be solved by increasing the head of the reservoir to 21.5 cm. It was also observed qualitatively that, in low voidage form, the cocoa-butter filled capillaries appeared somewhat smaller than their air-filled counterparts (less than 3 mm compared to less than 4 mm). It was also possible to create high-voidage cocoa-butter filled capillary extrudates, subject to the cocoa-butter head being high enough to supply molten cocoa butter at the increased rate.

Material 1 was successfully formed into capillary extrudates, of both high and low voidage, with either airfilled capillaries or cocoa butter-filled capillaries. Varying different voidages films were made, and it was observed that increasing levels of voidage led to increasing fragility. A representative figure for one of the high voidage air-cored films was between 35% and 40% and it is estimated that the very high voidage, highly fragile films, exceeded this.

Material 2 was formed from a mixture of 96% maltitol syrup, 2% gum Arabic, 2% water. Material 2 was shown to act in a similar manner to material 1, in that it was supplied in a large block that was required to be broken up mechanically into smaller granules before it could be fed into the extrusion line. Prior to extrusion experiments commencing, the extrusion die was disassembled and washed and the extruder was fed a hot water wash to dissolve any material 1 remaining within the extruder barrels or on the screw. After the water was purged from the extruder, the extruder was heated to 130° C. for between five and ten minutes to evaporate any remaining water. An early scoping experiment revealed that material 2 required higher extrusion temperatures than material 1; the final extrusion line temperature profile is shown in Table 3 below.

TABLE 3

Extruder temperature profile for material 2.

| Temperature zone | Label on FIG. 1 | Temperature (° C.) |
| --- | --- | --- |
| Barrel zone 1 | T1 | 115 |
| Barrel zone 2 | T2 | 115 |
| Barrel zone 3 | T3 | 115 |
| Die zone 1 | T4 | 115 |
| Die | T5 | 120 |

As with material 1, material 2 was starve-fed into the extruder. As with material 1, the screw speed was set to 40 rpm. Material 2 proved to be easy to extrude and capillary extrudates with air-filled capillaries were produced in both low and high voidage forms. Material 2 exhibited good melt strength, good drawing characteristics prior to solidifying and became brittle and glassy upon solidification. Again, this precluded the use of nip rollers to draw the material from the die and control the amount of draw down achieved, hence manual drawing was used in a similar way to material 1. In terms of restarting the extrusion line after an idle period, material 2 did not prove to be noticeably different to material 1, and the line restarted relatively easily. Due to the ease with which capillary extrudates were achieved, phase one was concluded relatively quickly to allow progression to phase two.

Phase two experiments were conducted with material 2 using cocoa butter heated to between 35° C. and 40° C. The head, h, of the cocoa butter reservoir was kept at 21.5 cm, and material 2 starve-fed into the extruder as described in the previous section. Successful extrusion of both low- and high-voidage micro capillary extrudate from material 2 containing completely filled cocoa-butter capillaries was achieved. A photograph comparing the cocoa-butter filled capillaries of material 2 to the air filled capillaries of material 1 is shown in FIG. 6. Crude optical analysis of a cross section of a piece of high-voidage material 2 revealed that the voidage was roughly 35% at minimum. It is likely this figure can be easily increased through optimisation of the protocol.

The observations for material 2 are similar to those from material 1. Low- and high-voidage capillary extrudates were formed, either containing cocoa-butter capillaries or air-filled capillaries, Crude optical analysis of a moderately high-voidage extrudate revealed that the void fraction was approximately 35%. Although, it is thought that the actual figure may have been higher. Increasing product voidage again led to increasing product fragility due to the capillary walls becoming very thin.

The objective of these first and second phase experiments were to provide proof-of-concept for the extrusion of capillary extridates from various candy materials. This was successful with both materials (material 1=40% sugar and 60% glucose, and material 2=96% maltitol syrup, 2% gum Arabic and 2% water). Low- and high-voidage capillary extrudates were formed containing both air-filled capillaries and cocoa-butter filled capillaries. It was estimated that a typical high-voidage extrudate contained roughly 35% to 40% voidage whether it was air filled or cocoa-butter filled.

Example 2

The third phase built upon the first two phases described in Example 1 and recreated the working environment with food grade equipment in a food grade environment. This food-grade setup extruded hard candy, chocolate and chewing gum with air, liquid and solid centres. This range of filled extrudates were made in a food grade environment and were consumed to investigate their edible properties.

The following edible materials were used in these experiments:

Chewing gum (uncoated Peppermint-Spearmint Higher flavour chewing gum pellets); hard candy, mint candy (Extra Strong Mints®, Jakemans® Old Favourites), fruit candy (Summer Fruits, Jakemans® Old Favourites), chocolate (milk chocolate (with 0, ½, 1, 2% added water), Cadbury® Dairy Milk® Buttons—when used molten, 2% PGPR was added to lower the melt viscosity for ease of use (c.f. legal limit of ½%)), compound chocolate (Plain Belgian Chocolate, SuperCook®), 72% Cook's Chocolate, Green & Black's®. Liquid fillings used in these experiments included: monopropylene glycol (Propane-1,2-diol, BP, EP, USE, Fisher Scientific®—selected for low viscosity, zero moisture, low flavour, and BP, EP & USE grade for oral use), Golden Syrup (partially inverted refiners syrup—Tate & Lyle®—selected for higher viscosity, food grade, shelf stability, and sweet flavour), Red Food Colouring (SuperCook®, UK), Blue Food Colouring (SuperCook®, UK). Lastly, a solid filling of cocoa butter obtained internally from a Cadbury Plc. site was also used in these experiments and this was selected because it is solid at room temperature and has low hot viscosity.

A Davis-Standard HPE-075 ¾" 24:1 single-screw extruder was used in these experiments. The extruder also included air-knives and a header tank. The screw was a simple conveying-compression-pumping all forward element design, with no mixing or reversing sections. The motor was 3 KW, geared to produce 0-100 rpm screw rotation. The feed throat was jacketed and supplied with flowing ambient water to prevent heat transfer from the barrel causing feed problems with sticky feedstuff. The barrel had three heating zones, each with a 1 KW heater and forced ambient air cooler. The standard extruder has a Eurotherm 3216 controller per barrel zone and one spare for the die (die controller connected to thermocouple input and standard 16A 240 v socket for up to 1 KW heater output).

At point of purchase, two additional die controllers, thermocouple inputs and heater outputs were specified to enable integrated control of the header tank containing filling material and the pipework connecting that header tank to the die. The die was an assembly of parts comprising a body with main die orifice of long thin rectangular shape, through which 19 interconnected nozzles (similar in size to hypodermic needles) also exited. The main body was heated and the nozzles led to an external fitting that could be opened to ambient air or could be connected to the heated, pressurized header tank. A bobbin shaped flange was constructed to mount the die assembly onto the extruder end flange.

The die was heated with 4×100 W ¼" cartridge heaters, and monitored by a K-type thermocouple probe. Initially these were controlled by a Eurotherm 3216 in a bespoke enclosure until the control and power wiring was transferred to a Eurotherm integrated into the extruder. The die assembly was earthed into the power outlet from the extruder.

The header-tank and the pipework connecting the header tank to the die were heated with two 100 W ribbon heaters initially controlled from a single analogue controller in a bespoke enclosure, and monitored by a single bare K-type thermocouple. These were later separated to two Eurotherm 3216s integrated into the extruder with two thermocouples and two power supplies. The header tank was earthed to the power outlet, whilst the pipework was plastic and did not need to be earthed.

Compressed air, BOC®, UK was regulated with series 8000 gas regulator and pressures used were 0-10 bar. The main use for the compressed air was to supply the air-knives.

Food Safe High-Tech Grease, and Food Safe Penetrating Oil from Solent Lubricants, Leicester, UK was used.

The capillary die was connected on the extruder endplate. Two opposed air knives were used to rapidly quench the extrudate emerging from the extrusion die, were placed above and below the die exit; these jets were connected via a valve to a compressed air line at 10 bar pressure. A schematic diagram showing the general layout of the extrusion line is shown in FIG. 1.

In use, the flow of molten material over the tips of the entrainment nozzles (hypodermic needles) caused a small area of low pressure to form at each needle tip. Each nozzle was connected together via internal channeling within the entrainment body. This, in turn, was connected outside the extrusion die to either air at room temperature and pressure or to a header tank containing a liquid that was at ambient or elevated temperature and pressure, with a hydraulic head of h. The header tank and the pipework connecting to the die were externally heated. A set of isolation valves were used to switch between either using an air feed to the entrainment body or a molten cocoa butter feed. This is shown schematically in FIG. 2.

The quench jets were used for the generation of the high-voidage material. It had been found during previous research that if the emerging extrudate was quenched very rapidly and subjected to a high drawing force, a higher voidage cross section could be obtained. Adjustment of the polymer and process conditions yielded voidages up to, and possibly in excess of, 60%.

Hard candy was pre-broken before introduction to the extruder. Particle size was not important—the extruder was found to take whole candies or dust. It was found that broken candies fed more evenly than whole pieces. All barrels and the die were set to 95° C. for fruit candy. Mint candy had tolerance to a wide range of temperatures and could run with barrels and die at 95°-110° C.

Screw speeds of 15-100 rpm were used in the experiments. Differences in product were minimal (except rate of production). Continuous, complete, transparent films with well formed capillaries could be produced optimisation of the protocol. The films could be filled and/or drawn without leaking. Product morphology was found to change with drawing speed and rate of cooling inline. Fast drawing with no cooling could thin the films to 1 mm wide with microscopic width and capillaries. Drawing with heavy cooling enlarged the voidage in the films.

In another test, uncoated gum pellets were reduced in size to approximately 3 mm to aid feeding into the extruder. This was done with freezing and a domestic food processor. Barrel and die temperatures of 58° C. resulted in the most contiguous product. This product had sufficient integrity to be filled with few leaks. It is likely that using gum base, in particular molten gum base, rather than whole gum would produce films with even greater integrity.

In a further test, chocolate was used as material for extrusion. To gain stable running conditions, the heaters and cooling fans of the extruder were electrically disabled. Direct temperature control was abandoned in favour of relying on the air conditioning of the laboratory. With these modifications the extruder barrel indicated an even 22° C. and it was simple to extrude capillary chocolate in a steady state using molten tempered Cadbury's Dairy Milk® chocolate.

As with hard candy extrusion, it was possible to draw the chocolate extrudate so as to alter the cross sectional geometry, and produce capillaries having diameters or widths of between 0.5 mm and 4 mm.

Air filling was achieved through a simple ambient air-bleed to the nozzles in the die and a cross section of the extrudate is shown in FIG. 8.

Monopropylene glycol filling was achieved at ambient temperature and pressure, with approximately 5 cm liquid depth in the header tank which was in turn approximately 10 cm higher than the die. Colour was added directly into the header tank as and when required.

Golden Syrup filling was achieved by heating the header tank and pipework to 78° C. to fill hard candy, and 58° C. to fill gum. Pressurisation of the header tank was required at the lower temperature to generate syrup flow. Again, colour was added directly into the header tank as and when required.

FIGS. 8-14 shows photographs of extrusions formed in the third phase of experiments. FIG. 8 shows a hard candy with an air fill. FIG. 9 shows a hard candy with a liquid fill. FIG. 9 shows a gum with an air fill. FIG. 10 shows a gum with a liquid fill. FIG. 11 shows a chocolate with an air fill. FIG. 12 shows a chocolate with an air fill as shown in FIG. 11, but in longitudinal cross section.

Confectionery products and methods of the invention have been shown for chocolate, hard candy and gum. The experiments of the third phase had shown a range of food materials that can also be used. It could therefore be deduced that any product normally solid at room temperature yet extrudable at elevated temperature and pressure could be formed into a capillary product such as chewy, gummy or jelly candies, for example. Products that show high extensional viscosity when warm may be drawn to alter their geometry and their outer to inner ratio.

It has also been shown that air, liquid and solid centres can be incorporated into capillary extrusions, providing the solid centre can be liquefied and is flowable.

It will be apparent to the skilled addressee that the capillary extrudate produced in the examples could be employed in confectionery in a number of ways. For example, a chocolate extrudate having capillaries filled with air could be used to manufacture a chocolate bar having a similar size to a regular bar, but lower in fat and sugar—as it contains less material. Alternatively, a chocolate extrudate could have capillaries filled with a liquid chocolate filling so as to provide an enhanced sensory pleasure. A further example may be a milk chocolate extrudate having capillaries filled with a dark chocolate filling, so as to produce a different flavour profile.

The extrudates of the present invention could be configured in a number of ways. For example, FIGS. 15A and 15B show an extrudate 100 having centre filled capillaries 102, where the extrudate is folded back on it self several times. Such a configuration would enable an extended release of centre fill during chewing. A chocolate élair could be formed having a chewy centre having liquid filled capillaries—where the chewy centre was a folded several times so as to enable the liquid fill to be released over an extended period.

FIG. 16, shows multiple layers of extrudate 120 being stacked on top of one another and each stack having a plurality of capillaries 122 with a centre filling. Such an arrangement could also be employed in a chewy confectionery.

FIGS. 17-28 illustrate a small number of confectionery products which can be made according to the present invention.

FIG. 17 shows a cylindrical confectionery product 200 having a circular cross-section. The confectionery product 200 incorporates an effervescing system so as to produce an enhanced sensory experience when it is consumed. The product is generally formed from an extruded soft candy material 202 which incorporates a first capillary 204 and a second capillary 206. The first capillary 204 contains a citric acid component, whereas the second capillary contains a bicarbonate component. When the product is consumed, the act of chewing mixes the citric acid component and the bicarbonate component together and both components react together so as to effervesce in the mouth.

FIG. 18 shows a cylindrical confectionery product 210 having a circular cross-section. The confectionery product 210 is a throat sweet and is generally formed from an extruded hard candy material 212. In a central portion of the product, there is provided a large capillary 214, surrounding which are a number of smaller, uniformly spaced capillaries 216 extending around the periphery of the product. The large capillary 214 contains a throat soothing component such as a mixture of honey and menthol, whilst the smaller capillaries 216 contain expectorants (such as ammonium chloride) and nasal decongestant (such as phenylpropanolamine). The candy material additionally contains other components used in throat sweets, such as anti-inflammatory agents. When the confectionery product is consumed, the hard candy 212 slowly degrades, which releases the anti-inflammatory agents so as to help reduce swelling in the mouth and throat. As the candy 212 degrades, the contents of the smaller capillaries 216 become exposed and the expectorant and decongestant are released into the mouth, which help to expel mucus and reduce the swelling of the nasal membranes. Lastly, further degradation of the candy 212 will lead to the release of the throat soothing component contained in the large central capillary 214 so as to further sooth the throat.

FIG. 19 shows a cylindrical confectionery product 220 having a circular cross section. The confectionery product is a combination breath-freshening and tooth-whitening gum. The product is formed of an extruded gum material 222 and has a number of uniformly spaced capillaries extend throughout its interior. The capillaries are filled with either a first material 224 (denoted in the Figure by means of a shaded dot) or a second material 226 (denoted in the Figure by means of a black dot). The extruded gum material contains a tooth-whitening component (such as hydrated silica), the first material 224 incorporates a breath freshening agent (such as a peppermint oil) and the second material 226 incorporates a cooling agent (such as N,2,3-trimethyl-2-isopropyl butanamide (WS-23)). When the confectionery material 220 is chewed, the tooth-whitening component in the gum helps to clean teeth, whilst the breath freshening and cooling agent in the capillaries are gradually released—thus providing a cool and refreshing feeling in the mouth.

FIG. 20 shows a cylindrical confectionery product 230 having a circular cross section. A number of capillaries are grouped together in fours (each group shown by a dotted line) and extend around the periphery of the product. The confectionery product is formed of an extruded chocolate 232. A first group of capillaries 234 contain fluid cocoa butter, whereas a second group of capillaries 236 contain a praline filling. Consumption of the confectionery product 230 provides an enhanced eating experience, due to the different textures of the chocolate, cocoa butter and praline. Both the cocoa butter and praline have an extended release profile as they are contained with individual capillaries within the chocolate.

FIG. 21 shows a cylindrical confectionery product 240 having a circular cross section. The confectionery product initiates with a warming sensation that shifts to a cooling sensation during consumption. In particular, in the embodiment shown in FIG. 21, the extruded body portion 242 is a hard candy including a warming agent, such as any of those set forth herein. A plurality of capillaries 244, such as 20-30 capillaries, are distributed throughout the hard candy body portion. The capillaries 244 are filled with a liquid fill material including a cooling agent, such as any of those set forth herein. The warming agent releases initially from the body portion as the hard candy product is consumed. However, after a period of time, the cooling agent is released from the capillaries, thereby providing a sequential release profile of warming followed by cooling.

FIG. 22 shows another cylindrical confectionery product 250 having a circular cross section. The confectionery product initiates with a cooling sensation that shifts to a warming sensation during consumption. In this embodiment, the extruded body portion 252 is a hard candy, such as a lozenge. A first group of capillaries 254 is distributed around the periphery of the body portion 252 and a second group of capillaries 256 is distributed interior to the first group 254. The first group of capillaries 254 is filled with a first liquid fill material including a cooling agent. The second group of capillaries 256 is filled with a second liquid fill material including a warming agent. The two groups of capillaries are essentially free of the opposing sensate. During consumption, the cooling agent is released from the first group of capillaries 254 first. After further consumption, the warming agent is released from the second, or interior, group of capillaries 256. The sequential release profile provides a shift from a cooling sensation to a warming sensation. As shown in the embodiment in FIG. 22, the first and second group of capillaries may have the same widths or diameters. In another embodiment, as shown in FIG. 23, the first and second groups of capillaries have different diameters. For instance, the first group of capillaries 264 in FIG. 23 has a larger diameter than the second group of capillaries 266. In such embodiment, the cooling sensation may have a greater intensity than the warming sensation as a larger amount of fill material containing more cooling agent is released from the outer group of capillaries.

FIG. 24 shows another cylindrical confectionery product 270 having a circular cross section. The confectionery product is a chewy candy including a center-fill region 272. A plurality of capillaries 274 are distributed around the periphery of the body portion and surrounding the center-fill region 272. The center-fill region 272 includes a liquid fill material including a warming agent. The capillaries are filled with another liquid fill material including a cooling agent. Upon consumption, the cooling agent is initially released from the capillaries, and then the warming agent is released from the center-fill region. The sequential release profile provides a shift from a cooling sensation to a warming sensation during consumption.

FIG. 25 shows another cylindrical confectionery product 280 having a circular cross section. The extruded body portion 282 is a sugar-free chewing gum composition, which is enveloped by a coating region 284. The coating region 284 is a sugar-free, panned coating including a combination of warming agents. A plurality of capillaries 286 are distributed throughout the body portion 282 and are filled with a liquid fill material including a combination of cooling agents. Upon consumption, there is an initial burst of warming sensation from the outer coating. During further mastication of the chewing gum, the cooling agents are released from the capillaries and the sensation shifts from warming to cooling, thereby providing a sequential release profile.

FIG. 26 shows another cylindrical confectionery product 290 having a circular cross section. The extruded body portion 292 is a sugared chewy candy composition including a sweet flavour, such as, for instance, peach flavour. Two groups of capillaries are distributed throughout the extruded body portion. The first group of capillaries 294 includes a liquid fill material including a savory flavour, such as, for instance, cream flavour. The second group of capillaries 296 contains a fill material including fibers and/or proteins. The confectionery product is designed to impart a sensation of satiety upon consumption. The sweet and savory flavours together provide a flavour profile that is sweet, creamy and indulgent. The fibers and/or proteins contained in the capillaries of the product impart a perception of being filled up to the consumer. Additionally, fibers and proteins are actives that can degrade when processed according to conventional confectionery manufacturing techniques. Incorporating such degradable actives into the capillaries of the product rather than the extruded body portion may alleviate such concerns. In combination, the sweet and savory flavour profile along with the fibers and/or proteins contained in the capillaries provides a confectionery product that can satisfy a feeling of hunger and thereby impart a perception of satiety to the consumer.

FIG. 27 shows a confectionery product 300 having a generally square cross section with rounded edges. The extruded body portion 302 is a chocolate composition including caffeine as an active. Two groups of capillaries are distributed throughout the body portion 302. The first group of capillaries 304 contain a liquid fill material including a caramel flavour, which is a sweet flavour. The second group of capillaries 306 contain a liquid fill material including a cream flavour, which is a savory flavour. The combination of the caramel, cream and chocolate flavors released during consumption along with the caffeine included in the product can satisfy a hunger craving and thereby impart a perception of satiety upon consumption.

FIG. 28 shows a confectionery product 310 having an ovular cross-section. The confectionery product in this embodiment is a dental cleaning chewing gum. The extruded body portion 312 is a sugar-free chewing gum composition with a sugar-free coating region 314 enveloping the product. The body portion includes a dental cleaning agent having a chemical mechanism of action, such as, for instance, a peroxide. The peroxide may be free or encapsulated. The peroxide is incorporated as a stain removing, or tooth whitening, agent. A plurality of capillaries 316 are distributed throughout the body portion of the chewing gum. The capillaries 316 include a second dental cleaning agent having a mechanical mechanism of action, such as, for instance, a foaming or effervescing agent. Upon consumption, the peroxide may be released from the body portion 312 of the chewing gum first. This may provide a pre-treatment step. Upon further mastication, the foaming or effervescing agent may be released from the capillaries 316. The foaming or effervescing agent provides a different mechanism of action for cleaning the tooth surface. This may enhance the cleaning efficacy of the product or at least a perception thereof to the consumer.

Although the body portion and capillaries may be depicted as uniform in shape and pattern in some embodiments described herein, it should be understood that the body portion and/or the capillaries may be non-uniform in some embodiments. There may be variations in the overall dimensions of the product, such as, for instance, the dimensions of the body portion, the capillaries, the wall thicknesses between each capillary and the outer wall thickness of the product. For example, in some embodiments, the mechanical process of extrusion and optional further manipulation of the extrudate, such as stretching, may create non-uniformities in the dimensions of the product. Such processes also may create random variations in the positioning of the capillaries. The capillaries accordingly may be irregularly positioned in some embodiments. In addition, the capillaries may be symmetrically disposed in the body portion or asymmetrically disposed in the body portion. In some embodiments, one group of capillaries may be symmetrically disposed and another group of capillaries may be asymmetrically disposed in the body portion.

The foregoing embodiments are not intended to limit the scope of protection afforded by the claims, but rather to describe examples as to how the invention may be put into practice.

The invention claimed is:

1. A confectionery product comprising
an extruded body portion, the body portion having a plurality of capillaries disposed therein, a first group of said capillaries being at least partially filled with a supersaturated polyol solution comprising water and a polyol, and a second group of said capillaries being at least partially filled with seed crystals of the polyol, wherein said first group of capillaries and said second group of capillaries have different diameters, and being adapted to provide sequential release profiles.

2. The confectionery product of claim 1, comprising from 5 to 50 of said capillaries.

3. The confectionery product of claim 2, comprising from 10 to 40 of said capillaries.

4. The confectionery product of claim 3, comprising from 20 to 40 of said capillaries.

5. The confectionery product of claim 1, wherein said capillaries have an average diameter of about 0.1-5 millimeters.

6. The confectionery product of claim 1, wherein the first group of said capillaries is distributed around the periphery of the body portion and the second group of said capillaries is distributed interior to said first group.

7. The confectionery product of claim 1, wherein said first group of capillaries has a larger diameter than said second group of capillaries.

8. The confectionery product of claim 1, further comprising a center-fill region, said capillaries being distributed around the periphery of the body portion and surrounding said center-fill region.

9. The confectionery product of claim 8, wherein said center-fill region comprises a liquid-fill composition.

10. The confectionery product of claim 8, wherein said center-fill region comprises a chewing gum composition.

11. The confectionery product of claim 1, further comprising a coating region enveloping said extruded body portion.

12. The confectionery product of claim 1, wherein said extruded body portion is selected from the group consisting of hard candy, chewy candy, chewing gum and chocolate.

13. A process for manufacturing a confectionery product comprising an extruded body portion having a plurality of capillaries disposed therein, the process comprising the steps of:
a) extruding an extrudable confectionery material with a plurality of capillaries disposed therein; and
b) at least partially filling a first group of said capillaries with a supersaturated polyol solution comprising water and a polyol, and a second group of said capillaries with seed crystals of the polyol;
wherein said first group of capillaries and said second group of capillaries have different diameters and said product being adapted to provide sequential release profiles.

* * * * *